(12) United States Patent
Landau et al.

(10) Patent No.: US 7,314,483 B2
(45) Date of Patent: Jan. 1, 2008

(54) STENT GRAFT WITH BRANCH LEG

(75) Inventors: George D. Landau, Verona, NJ (US);
Marc Ramer, Weston, FL (US);
Kenneth S. Solovay, Weston, FL (US)

(73) Assignee: Cordis Corp., Miami Lakes, FL (US)

( * ) Notice: Subject to any disclaimer, the term of this patent is extended or adjusted under 35 U.S.C. 154(b) by 0 days.

(21) Appl. No.: 10/041,369

(22) Filed: Jan. 8, 2002

(65) Prior Publication Data

US 2002/0058986 A1    May 16, 2002

Related U.S. Application Data

(63) Continuation-in-part of application No. 09/714,080, filed on Nov. 16, 2000, now Pat. No. 6,656,215, and a continuation-in-part of application No. 09/714,093, filed on Nov. 16, 2000, now abandoned, and a continuation-in-part of application No. 09/714,078, filed on Nov. 16, 2000, now Pat. No. 6,626,938, and a continuation-in-part of application No. 09/714,079, filed on Nov. 16, 2000, now Pat. No. 6,482,227.

(51) Int. Cl.
*A61F 2/06* (2006.01)

(52) U.S. Cl. .................................. 623/1.35; 623/1.16

(58) Field of Classification Search ............... 623/1.35, 623/1.16, 1.36
See application file for complete search history.

(56) References Cited

U.S. PATENT DOCUMENTS

| | | | |
|---|---|---|---|
| 3,142,067 A | 7/1964 | Liebig | |
| 3,585,707 A | 6/1971 | Stevens | |
| 3,657,744 A | 4/1972 | Ersek | |
| 4,140,126 A | 2/1979 | Choudhury | |
| 4,169,464 A | 10/1979 | Obrez | |

(Continued)

FOREIGN PATENT DOCUMENTS

DE    D3205942 A1    9/1983

(Continued)

OTHER PUBLICATIONS

Partial European Search Report EP 03250103 dated May 21, 2003 which corresponds to related U.S. Appl. No. 10/041,142.

(Continued)

*Primary Examiner*—Corrine McDermott
*Assistant Examiner*—Cheryl Miller

(57) ABSTRACT

The present invention is directed to a system, apparatus, and method for treating, repairing, and/or replacing an aneurysm, preferably an aortic aneurysm, and most preferably, an abdominal aortic aneurysm. The systems, devices, and methods of the present invention include a first prosthesis or stent gasket, and at least one second prosthesis for bypassing the aneurysm. In preferred embodiments, the second prosthesis includes a branch leg that may be disposed and anchored in an either a cross artery or a downstream artery to facilitate fluid flow. In other preferred embodiments, at least one third prosthesis is provided for establishing a fluid flow channel through a second diseased artery to bypass an aneurysm disposed therein. In accordance with the invention, the first artery may be the abdominal aorta and the second artery may be an iliac artery.

5 Claims, 16 Drawing Sheets

U.S. PATENT DOCUMENTS

| | | |
|---|---|---|
| 4,187,390 A | 2/1980 | Gore |
| 4,317,451 A | 3/1982 | Cerwin et al. |
| 4,441,216 A | 4/1984 | Ionescu et al. |
| RE31,618 E | 7/1984 | Mano |
| 4,503,569 A | 3/1985 | Dotter |
| 4,545,082 A | 10/1985 | Hood |
| 4,553,545 A | 11/1985 | Maass |
| 4,562,596 A | 1/1986 | Kornberg |
| 4,570,006 A | 2/1986 | Fujii et al. |
| 4,580,568 A | 4/1986 | Gianturco |
| 4,604,762 A | 8/1986 | Robinson |
| 4,617,932 A | 10/1986 | Kornberg |
| 4,655,771 A | 4/1987 | Wallsten |
| 4,665,906 A | 5/1987 | Jervis |
| 4,681,110 A | 7/1987 | Wiktor |
| 4,705,517 A | 11/1987 | DiPisa, Jr. |
| 4,728,328 A | 3/1988 | Hughes |
| 4,731,073 A | 3/1988 | Robinson |
| 4,732,152 A | 3/1988 | Wallsten |
| 4,733,665 A | 3/1988 | Palmaz |
| 4,739,762 A | 4/1988 | Palmaz |
| 4,769,029 A | 9/1988 | Patel |
| 4,776,337 A | 10/1988 | Palmaz |
| 4,784,137 A | 11/1988 | Kulik et al. |
| 4,787,899 A | 11/1988 | Lazarus |
| 4,800,882 A | 1/1989 | Gianturco |
| 4,822,341 A | 4/1989 | Colone |
| 4,850,999 A | 7/1989 | Planck |
| 4,856,516 A | 8/1989 | Hillstead |
| 4,875,480 A | 10/1989 | Imbert |
| 4,886,062 A | 12/1989 | Wiktor |
| 4,907,336 A | 3/1990 | Gianturco |
| 4,913,141 A | 4/1990 | Hillstead |
| 4,925,445 A | 5/1990 | Sakamoto |
| 4,950,227 A | 8/1990 | Savin |
| 4,955,899 A | 9/1990 | Della Corna |
| 4,969,458 A | 11/1990 | Wiktor |
| 4,990,131 A | 2/1991 | Dardik |
| 4,990,151 A | 2/1991 | Wallsten |
| 4,990,155 A | 2/1991 | Wilkoff |
| 4,994,071 A | 2/1991 | MacGregor |
| 5,015,253 A | 5/1991 | MacGregor |
| 5,019,085 A | 5/1991 | Hillstead |
| 5,026,377 A | 6/1991 | Burton |
| 5,035,694 A | 7/1991 | Kasprzyk et al. |
| 5,035,706 A | 7/1991 | Giantureo |
| 5,041,126 A | 8/1991 | Gianturco |
| 5,045,072 A | 9/1991 | Castillo |
| 5,064,435 A | 11/1991 | Porter |
| 5,078,726 A | 1/1992 | Kreamer |
| 5,084,065 A | 1/1992 | Weldon |
| 5,100,422 A | 3/1992 | Berguer et al. |
| 5,102,417 A | 4/1992 | Palmaz |
| 5,104,399 A | 4/1992 | Lazarus |
| 5,104,400 A | 4/1992 | Berguer |
| 5,104,404 A | 4/1992 | Wolff |
| 5,114,423 A | 5/1992 | Kasprzyk et al. |
| 5,116,365 A | 5/1992 | Hillstead |
| 5,122,154 A | 6/1992 | Rhodes |
| 5,123,917 A | 6/1992 | Lee |
| 5,131,908 A | 7/1992 | Dardik et al. |
| 5,133,732 A | 7/1992 | Wiktor |
| 5,135,536 A | 8/1992 | Hillstead |
| 5,151,105 A | 9/1992 | Kwan-Gett |
| 5,152,782 A | 10/1992 | Kowligi |
| 5,156,620 A | 10/1992 | Pigott |
| 5,159,920 A | 11/1992 | Cordon |
| 5,163,951 A | 11/1992 | Pinchuk |
| 5,163,958 A | 11/1992 | Pinchuk |
| 5,171,262 A | 12/1992 | MacGregor |
| 5,176,660 A | 1/1993 | Truckai |
| 5,178,618 A | 1/1993 | Kandarpa |
| 5,192,297 A | 3/1993 | Trescony et al. |
| 5,192,307 A | 3/1993 | Wall |
| 5,195,984 A | 3/1993 | Schatz |
| 5,207,695 A | 5/1993 | Trout, III |
| 5,211,658 A | 5/1993 | Clouse |
| 5,217,483 A | 6/1993 | Tower |
| 5,219,355 A | 6/1993 | Parodi |
| 5,222,971 A | 6/1993 | Willard et al. |
| 5,236,447 A | 8/1993 | Kubo |
| 5,246,445 A | 9/1993 | Yachia et al. |
| 5,246,452 A | 9/1993 | Sinnott |
| 5,254,107 A | 10/1993 | Soltesz |
| 5,258,021 A | 11/1993 | Duran |
| 5,258,027 A | 11/1993 | Berghaus |
| 5,266,073 A | 11/1993 | Wall |
| 5,275,622 A | 1/1994 | Lazarus et al. |
| 5,282,823 A | 2/1994 | Schwartz et al. |
| 5,282,824 A | 2/1994 | Gianturco |
| 5,282,847 A | 2/1994 | Trescony et al. |
| 5,282,860 A | 2/1994 | Matsuno |
| 5,290,305 A | 3/1994 | Inoue |
| 5,292,331 A | 3/1994 | Boneau |
| 5,304,197 A | 4/1994 | Pinchuk |
| 5,304,200 A | 4/1994 | Spaulding |
| 5,306,294 A | 4/1994 | Winston |
| 5,314,444 A | 5/1994 | Gianturco |
| 5,314,472 A | 5/1994 | Fontaine |
| 5,316,023 A | 5/1994 | Palmaz |
| 5,318,535 A | 6/1994 | Miraki |
| 5,321,109 A | 6/1994 | Bosse |
| 5,330,490 A | 7/1994 | Wilk |
| 5,330,500 A | 7/1994 | Song |
| 5,330,528 A | 7/1994 | Lazim |
| 5,334,201 A | 8/1994 | Cowan |
| 5,334,301 A | 8/1994 | Heinke et al. |
| 5,342,387 A | 8/1994 | Summersq |
| 5,354,257 A | 10/1994 | Roubin et al. |
| 5,354,308 A | 10/1994 | Simon et al. |
| 5,358,493 A | 10/1994 | Schweich, Jr. et al. |
| 5,360,443 A | 11/1994 | Barone |
| 5,366,473 A | 11/1994 | Winston et al. |
| 5,366,504 A | 11/1994 | Andersen et al. |
| 5,370,683 A | 12/1994 | Fontaine |
| 5,370,691 A | 12/1994 | Samson |
| 5,375,612 A | 12/1994 | Cottenceau et al. |
| 5,376,112 A | 12/1994 | Duran |
| 5,380,328 A | 1/1995 | Morgan |
| 5,382,261 A | 1/1995 | Palmaz |
| 5,383,927 A | 1/1995 | DeGoicoechea |
| 5,387,235 A | 2/1995 | Chuter |
| 5,389,106 A | 2/1995 | Tower |
| 5,395,390 A | 3/1995 | Simon et al. |
| 5,397,345 A | 3/1995 | Lazarus |
| 5,397,355 A | 3/1995 | Marin et al. |
| 5,403,341 A | 4/1995 | Solar |
| 5,405,322 A | 4/1995 | Lennox et al. |
| 5,405,377 A | 4/1995 | Cragg |
| 5,411,507 A | 5/1995 | Heckele |
| 5,411,549 A | 5/1995 | Peters |
| 5,417,708 A | 5/1995 | Hall et al. |
| 5,419,324 A | 5/1995 | Dillow |
| D359,802 S | 6/1995 | Fontaine |
| 5,421,955 A | 6/1995 | Lau et al. |
| 5,423,885 A | 6/1995 | Williams |
| 5,439,446 A | 8/1995 | Barry |
| 5,441,515 A | 8/1995 | Khosravi et al. |
| 5,441,516 A | 8/1995 | Wang et al. |
| 5,443,477 A | 8/1995 | Marin et al. |
| 5,443,496 A | 8/1995 | Schwartz et al. |
| 5,443,498 A | 8/1995 | Fontaine |
| 5,443,500 A | 8/1995 | Sigwart |
| 5,449,372 A | 9/1995 | Schmaltz et al. |

| | | | | | |
|---|---|---|---|---|---|
| 5,449,373 A | 9/1995 | Pinchasik et al. | 5,685,847 A | 11/1997 | Barry |
| 5,449,382 A | 9/1995 | Dayton | 5,693,083 A | 12/1997 | Baker et al. |
| 5,453,090 A | 9/1995 | Martinez et al. | 5,693,084 A | 12/1997 | Chuter |
| 5,453,235 A | 9/1995 | Calcote | 5,693,085 A | 12/1997 | Limon et al. |
| 5,456,713 A | 10/1995 | Chuter | 5,693,086 A | 12/1997 | Goicoechea et al. |
| 5,466,509 A | 11/1995 | Kowligi | 5,695,517 A | 12/1997 | Marin et al. |
| 5,468,138 A | 11/1995 | Bosse | 5,697,948 A | 12/1997 | Marin et al. |
| 5,476,506 A | 12/1995 | Lunn | 5,697,971 A | 12/1997 | Fischell et al. |
| 5,480,423 A | 1/1996 | Ravenscroft | 5,700,285 A | 12/1997 | Myers et al. |
| 5,484,444 A | 1/1996 | Braunchweiler | 5,702,418 A | 12/1997 | Ravenscroft |
| 5,489,295 A | 2/1996 | Piplani et al. | 5,713,917 A | 2/1998 | Leonhardt et al. |
| 5,496,365 A | 3/1996 | Fontaine et al. | 5,716,365 A | 2/1998 | Goicoechea et al. |
| 5,507,767 A | 4/1996 | Maeda et al. | 5,716,395 A | 2/1998 | Myers et al. |
| 5,507,769 A | 4/1996 | Marin | 5,718,159 A | 2/1998 | Thompson |
| 5,507,771 A | 4/1996 | Gianturco | 5,718,724 A | 2/1998 | Goicoechea et al. |
| 5,507,995 A | 4/1996 | Schweich, Jr. et al. | 5,720,735 A | 2/1998 | Dorros |
| 5,512,229 A | 4/1996 | Bosse | 5,720,776 A | 2/1998 | Chuter et al. |
| 5,522,880 A | 6/1996 | Barone | 5,723,003 A | 3/1998 | Winston et al. |
| 5,522,881 A | 6/1996 | Lentz | 5,723,004 A | 3/1998 | Dereume et al. |
| 5,522,882 A | 6/1996 | Gaterud | 5,725,534 A | 3/1998 | Rasmussen |
| 5,527,354 A | 6/1996 | Fontaine et al. | 5,725,568 A | 3/1998 | Hastings |
| 5,549,662 A | 8/1996 | Fordenbacher | 5,725,570 A | 3/1998 | Heath |
| 5,549,663 A | 8/1996 | Cottone, Jr. | 5,728,065 A | 3/1998 | Follmer et al. |
| 5,562,698 A | 10/1996 | Parker | 5,728,068 A | 3/1998 | Leone et al. |
| 5,562,724 A | 10/1996 | Vorwerk | 5,728,131 A | 3/1998 | Frantzen et al. |
| 5,562,726 A | 10/1996 | Chuter | 5,728,313 A | 3/1998 | Ritter et al. |
| 5,569,295 A | 10/1996 | Lam | 5,733,328 A | 3/1998 | Fordenbacher |
| 5,571,170 A | 11/1996 | Palmaz | 5,735,892 A | 4/1998 | Myers et al. |
| 5,571,171 A | 11/1996 | Barone | 5,746,709 A | 5/1998 | Rom et al. |
| 5,571,173 A | 11/1996 | Parodi | 5,749,880 A | 5/1998 | Banas |
| 5,578,071 A | 11/1996 | Parodi | 5,749,920 A | 5/1998 | Quiachon et al. |
| 5,578,072 A | 11/1996 | Barone | 5,749,921 A | 5/1998 | Lenker et al. |
| 5,591,196 A | 1/1997 | Marin et al. | 5,752,966 A | 5/1998 | Chang |
| 5,591,197 A | 1/1997 | Orth et al. | 5,755,734 A | 5/1998 | Richter et al. |
| 5,591,228 A | 1/1997 | Edoga | 5,755,735 A | 5/1998 | Richter et al. |
| 5,591,229 A | 1/1997 | Parodi | 5,755,770 A | 5/1998 | Ravenscroft |
| 5,593,412 A | 1/1997 | Martinez et al. | 5,755,771 A | 5/1998 | Penn et al. |
| 5,607,444 A | 3/1997 | Lam | 5,755,772 A | 5/1998 | Evans et al. |
| 5,607,464 A | 3/1997 | Trescony et al. | 5,755,773 A | 5/1998 | Evans et al. |
| 5,609,624 A | 3/1997 | Kalis | 5,755,777 A | 5/1998 | Chuter |
| 5,609,625 A | 3/1997 | Piplani et al. | 5,758,562 A | 6/1998 | Thompson |
| 5,609,627 A | 3/1997 | Goicoechea et al. | 5,760,006 A | 6/1998 | Shank et al. |
| 5,617,878 A | 4/1997 | Taheri | 5,766,201 A | 6/1998 | Ravenscroft et al. |
| 5,618,300 A | 4/1997 | Marin et al. | 5,769,882 A | 6/1998 | Fogarty et al. |
| 5,628,783 A | 5/1997 | Quiachon et al. | 5,769,885 A | 6/1998 | Quiachon et al. |
| 5,628,786 A | 5/1997 | Banas | 5,776,180 A | 7/1998 | Goicoechea et al. |
| 5,628,788 A | 5/1997 | Pinchuk | 5,782,765 A | 7/1998 | Jonkman |
| 5,632,763 A | 5/1997 | Glastra | 5,782,906 A | 7/1998 | Marshall et al. |
| 5,632,778 A | 5/1997 | Goldstein | 5,782,909 A | 7/1998 | Quiachon et al. |
| 5,634,941 A | 6/1997 | Winston et al. | 5,788,626 A | 8/1998 | Thompson |
| 5,639,278 A | 6/1997 | Dereume et al. | 5,797,953 A | 8/1998 | Tekulve |
| 5,641,443 A | 6/1997 | Calcote et al. | 5,800,456 A | 9/1998 | Maeda et al. |
| 5,643,312 A | 7/1997 | Fischell et al. | 5,800,508 A | 9/1998 | Goicoechea et al. |
| 5,645,559 A | 7/1997 | Hachtman | 5,800,516 A | 9/1998 | Fine et al. |
| 5,649,952 A | 7/1997 | Lam | 5,800,518 A | 9/1998 | Piplani et al. |
| 5,653,743 A * | 8/1997 | Martin ............... 623/1 | 5,800,520 A | 9/1998 | Fogarty et al. |
| 5,653,745 A | 8/1997 | Trescony et al. | 5,810,870 A | 9/1998 | Myers et al. |
| 5,653,747 A | 8/1997 | Dereume | 5,824,036 A | 10/1998 | Lauterjung |
| 5,662,700 A | 9/1997 | Lazarus | 5,824,037 A | 10/1998 | Fogarty et al. |
| 5,662,703 A | 9/1997 | Yurek et al. | 5,824,039 A | 10/1998 | Piplani et al. |
| 5,667,523 A | 9/1997 | Bynon | 5,824,040 A | 10/1998 | Cox et al. |
| 5,669,924 A | 9/1997 | Shaknovich | 5,824,041 A | 10/1998 | Lenker et al. |
| 5,669,936 A | 9/1997 | Lazarus | 5,824,042 A | 10/1998 | Lombardi et al. |
| 5,674,241 A | 10/1997 | Bley | 5,824,043 A | 10/1998 | Cottone, Jr. |
| 5,674,276 A | 10/1997 | Andersen et al. | 5,824,044 A | 10/1998 | Yazici et al. |
| 5,676,696 A | 10/1997 | Marcade | 5,824,046 A | 10/1998 | Smith et al. |
| 5,676,697 A | 10/1997 | McDonald | 5,824,054 A | 10/1998 | Khosravi et al. |
| 5,681,345 A | 10/1997 | Euteneuer et al. | 5,824,055 A | 10/1998 | Spiridigliozzi et al. |
| 5,681,346 A | 10/1997 | Orth et al. | 5,827,310 A | 10/1998 | Marin et al. |
| 5,683,448 A | 11/1997 | Cragg | 5,827,320 A | 10/1998 | Richter et al. |
| 5,683,449 A | 11/1997 | Marcade | 5,827,327 A | 10/1998 | McHaney et al. |
| 5,683,450 A | 11/1997 | Goicoechea et al. | 5,830,229 A | 11/1998 | Konya et al. |
| 5,683,451 A | 11/1997 | Lenker et al. | 5,833,651 A | 11/1998 | Donovan et al. |

| | | | | | | |
|---|---|---|---|---|---|---|
| 5,840,011 A | 11/1998 | Landgrebe et al. | 6,086,577 A | 7/2000 | Ken et al. | |
| 5,843,031 A | 12/1998 | Hermann et al. | 6,086,611 A | 7/2000 | Duffy et al. | |
| 5,843,120 A | 12/1998 | Israel | 6,090,127 A | 7/2000 | Globerman | |
| 5,843,158 A | 12/1998 | Lenker et al. | 6,090,128 A | 7/2000 | Douglas | |
| 5,843,160 A | 12/1998 | Rhodes | 6,090,133 A | 7/2000 | Richter et al. | |
| 5,855,598 A | 1/1999 | Pinchuk | 6,093,199 A | 7/2000 | Brown et al. | |
| 5,857,998 A | 1/1999 | Barry | 6,097,978 A | 8/2000 | Demarais et al. | |
| 5,858,556 A | 1/1999 | Eckert | 6,099,558 A | 8/2000 | White et al. | |
| 5,860,998 A | 1/1999 | Robinson et al. | 6,099,560 A | 8/2000 | Penn et al. | |
| 5,861,027 A | 1/1999 | Trapp | 6,102,938 A | 8/2000 | Evans et al. | |
| 5,868,777 A | 2/1999 | Lam | 6,102,940 A | 8/2000 | Robichon | |
| 5,871,537 A | 2/1999 | Holman et al. | 6,102,942 A | 8/2000 | Ahari | |
| 5,871,538 A | 2/1999 | Dereume | 6,110,191 A | 8/2000 | Dehdashtian et al. | |
| 5,876,397 A | 3/1999 | Edelman et al. | 6,110,198 A | 8/2000 | Fogarty et al. | |
| 5,876,449 A | 3/1999 | Starck et al. | 6,117,117 A | 9/2000 | Mauch | |
| 5,893,868 A | 4/1999 | Hanson et al. | 6,117,156 A | 9/2000 | Richter et al. | |
| 5,893,887 A | 4/1999 | Jayaraman | 6,117,157 A | 9/2000 | Tekulve | |
| 5,899,890 A | 5/1999 | Chiang et al. | 6,117,166 A | 9/2000 | Winston et al. | |
| 5,902,308 A | 5/1999 | Murphy | 6,117,167 A | 9/2000 | Goicoechea et al. | |
| 5,904,713 A | 5/1999 | Leschinsky | 6,123,722 A | 9/2000 | Fogarty et al. | |
| 5,906,619 A | 5/1999 | Olson et al. | 6,126,685 A | 10/2000 | Lenker et al. | |
| 5,906,640 A | 5/1999 | Penn et al. | 6,129,746 A | 10/2000 | Keith | |
| 5,906,641 A | 5/1999 | Thompson et al. | 6,129,754 A | 10/2000 | Hanson et al. | |
| 5,908,448 A | 6/1999 | Roberts et al. | 6,129,756 A | 10/2000 | Kugler et al. | |
| 5,916,263 A | 6/1999 | Goicoechea et al. | 6,132,450 A | 10/2000 | Hanson et al. | |
| 5,916,264 A | 6/1999 | Von Oepen | 6,132,459 A | 10/2000 | Piplani et al. | |
| 5,919,224 A | 7/1999 | Thompson et al. | 6,162,246 A | 12/2000 | Barone | |
| 5,928,260 A | 7/1999 | Chin et al. | 6,183,509 B1 | 2/2001 | Dibie | |
| 5,935,667 A | 8/1999 | Calcote | 6,203,568 B1 | 3/2001 | Lombardi et al. | |
| 5,938,696 A | 8/1999 | Goicoechea et al. | 6,210,429 B1 * | 4/2001 | Vardi et al. | 623/1.11 |
| 5,944,726 A | 8/1999 | Blaeser et al. | 6,214,040 B1 | 4/2001 | Jayaraman | |
| 5,944,750 A | 8/1999 | Tanner et al. | 6,224,609 B1 * | 5/2001 | Ressemann et al. | 606/108 |
| 5,951,599 A | 9/1999 | McCrory | 6,245,099 B1 | 6/2001 | Edwin et al. | |
| 5,954,693 A | 9/1999 | Barry | 6,270,525 B1 * | 8/2001 | Letendre et al. | 623/1.35 |
| 5,957,973 A | 9/1999 | Quiachon et al. | 6,287,335 B1 | 9/2001 | Drasler et al. | |
| 5,957,974 A | 9/1999 | Thompson et al. | 6,293,965 B1 * | 9/2001 | Berg et al. | 623/1.13 |
| 5,961,548 A | 10/1999 | Shmulewitz | 6,296,863 B1 | 10/2001 | Trogolo et al. | |
| 5,968,069 A | 10/1999 | Dusbabek et al. | 6,299,634 B1 | 10/2001 | Bergeron | |
| 5,968,088 A | 10/1999 | Hansen et al. | 6,302,906 B1 | 10/2001 | Goicoechea et al. | |
| 5,980,565 A | 11/1999 | Jayaraman | 6,306,164 B1 | 10/2001 | Kujawski | |
| 5,993,481 A | 11/1999 | Marcade et al. | 6,325,819 B1 | 12/2001 | Pavenik et al. | |
| 6,007,543 A | 12/1999 | Ellis et al. | 6,325,820 B1 | 12/2001 | Khosravi et al. | |
| 6,015,431 A | 1/2000 | Thornton et al. | 6,325,823 B1 * | 12/2001 | Horzewski et al. | 623/1.16 |
| 6,015,432 A | 1/2000 | Rakos et al. | 6,325,826 B1 * | 12/2001 | Vardi et al. | 623/1.35 |
| 6,016,810 A | 1/2000 | Ravenscroft | 6,331,188 B1 | 12/2001 | Lau et al. | |
| 6,016,848 A | 1/2000 | Egres, Jr. | 6,334,868 B1 | 1/2002 | Ham | |
| 6,017,363 A | 1/2000 | Hojeibane | 6,344,056 B1 | 2/2002 | Dehdashtian et al. | |
| 6,017,364 A | 1/2000 | Lazarus | 6,352,554 B2 | 3/2002 | De Paulis | |
| 6,019,778 A | 2/2000 | Wilson et al. | 6,361,557 B1 | 3/2002 | Gittings et al. | |
| 6,019,786 A | 2/2000 | Thompson | 6,409,756 B1 | 6/2002 | Murphy | |
| 6,024,763 A | 2/2000 | Lenker et al. | 6,468,301 B1 * | 10/2002 | Amplatz et al. | 623/1.13 |
| 6,027,526 A | 2/2000 | Limon et al. | 6,520,988 B1 * | 2/2003 | Colombo et al. | 623/1.35 |
| 6,027,529 A | 2/2000 | Roychowdhury et al. | 6,524,336 B1 | 2/2003 | Papazolgou et al. | |
| 6,030,413 A | 2/2000 | Lazarus | 6,576,009 B2 * | 6/2003 | Ryan et al. | 623/1.35 |
| 6,030,415 A | 2/2000 | Chuter | 6,596,023 B1 | 7/2003 | Nunez et al. | |
| 6,033,435 A | 3/2000 | Penn et al. | 6,648,913 B1 | 11/2003 | Yee et al. | |
| 6,036,697 A | 3/2000 | DiCaprio | 2001/0014823 A1 | 8/2001 | Petrick | |
| 6,036,723 A | 3/2000 | Anidjar et al. | 2002/0052648 A1 * | 5/2002 | McGuckin, Jr. et al. | |
| 6,036,725 A | 3/2000 | Avellanet | 2002/0156521 A1 | 10/2002 | Ryan et al. | |
| 6,039,749 A | 3/2000 | Marin et al. | 2002/0193873 A1 * | 12/2002 | Brucker et al. | 623/1.35 |
| 6,039,758 A | 3/2000 | Quiachon et al. | 2003/0097169 A1 * | 5/2003 | Brucker et al. | 623/1.11 |
| 6,048,356 A | 4/2000 | Ravenscroft et al. | | | | |
| 6,051,020 A | 4/2000 | Goicoechea et al. | | | | |

FOREIGN PATENT DOCUMENTS

| | | |
|---|---|---|
| 6,056,775 A | 5/2000 | Borghi et al. |
| 6,059,821 A | 5/2000 | Anidjar et al. | 
| 6,059,823 A | 5/2000 | Holman et al. |
| 6,059,824 A | 5/2000 | Taheri |
| 6,063,111 A | 5/2000 | Hieshima et al. |
| 6,068,655 A | 5/2000 | Seguin et al. |
| 6,070,589 A | 6/2000 | Keith et al. |
| 6,071,307 A | 6/2000 | Rhee et al. |
| 6,077,273 A | 6/2000 | Euteneuer et al. |
| 6,078,832 A | 6/2000 | Lenker et al. |

| | | |
|---|---|---|
| EP | 0 480 667 A1 | 4/1992 |
| EP | 0 540 290 A3 | 5/1993 |
| EP | 0 579 523 B1 | 1/1994 |
| EP | 0579523 A1 | 1/1994 |
| EP | 0 615 769 A1 | 9/1994 |
| EP | 0657147 A2 | 10/1994 |
| EP | 0 666 066 A | 8/1995 |
| EP | 0686379 B1 | 12/1995 |
| EP | 734698 A2 | 10/1996 |

| | | | | | | |
|---|---|---|---|---|---|---|
| EP | 783873 | A2 | 7/1997 | JP | 7100210 A | 4/1995 |
| EP | 800801 | A1 | 10/1997 | JP | 9724081 A1 | 7/1997 |
| EP | 830853 | A1 | 3/1998 | JP | 6 86827 A | 6/1998 |
| EP | 832616 | A1 | 4/1998 | JP | 9853761 A1 | 12/1998 |
| EP | 0855170 | A2 | 7/1998 | WO | 8704935 A1 | 8/1987 |
| EP | 0 861 638 | A2 | 9/1998 | WO | 9516406 A1 | 6/1995 |
| EP | 880948 | A1 | 12/1998 | WO | 9521592 A1 | 8/1995 |
| EP | 0 904 745 | A2 | 3/1999 | WO | 9626689 A1 | 9/1996 |
| EP | 0928606 | A1 | 7/1999 | WO | WO 96/32077 A1 | 10/1996 |
| EP | 937442 | A2 | 8/1999 | WO | 96/34580 A1 | 11/1996 |
| EP | 0947179 | A2 | 10/1999 | WO | 9725000 A1 | 7/1997 |
| EP | 1000590 | A1 | 5/2000 | WO | 9733532 A2 | 9/1997 |
| EP | 1 086 665 | A | 3/2001 | WO | WO 97 33532 A | 9/1997 |
| EP | 1 208 817 | A | 5/2002 | WO | 9807389 A1 | 2/1998 |
| EP | 1 212 989 | A2 | 6/2002 | WO | 98/19628 A1 | 5/1998 |
| EP | 1 212 990 | A | 6/2002 | WO | 9823322 A1 | 6/1998 |
| FR | 0 566 807 | A1 | 2/1924 | WO | 9836709 A1 | 8/1998 |
| FR | 2733682 | A1 | 11/1996 | WO | 9908744 A1 | 2/1999 |
| FR | 2740346 | A1 | 4/1997 | WO | 9911199 A1 | 3/1999 |
| FR | 2743293 | A1 | 7/1997 | WO | WO 01 74270 A | 10/2001 |
| FR | 2 777 450 | A | 10/1999 | WO | WO 02/26165 A1 | 4/2002 |
| GB | 662307 | A | 9/1948 | | | |
| GB | 1 205 743 | | 9/1970 | | | |
| JP | 5524095 | A | 2/1980 | | | |
| JP | 60220030 | A | 11/1985 | | | |
| JP | 62231657 | A | 3/1988 | | | |
| JP | 4064367 | A | 2/1992 | | | |
| JP | 4263852 | A | 4/1992 | | | |
| JP | 5076603 | A | 3/1993 | | | |
| JP | 5 269199 | A | 10/1993 | | | |
| JP | 7529 | A | 10/1994 | | | |
| JP | 6282730 | A | 10/1994 | | | |
| JP | 7 24072 | A | 1/1995 | | | |

OTHER PUBLICATIONS

Partial European Search Report EP 03250109 dated Jun. 13, 2003.
EPO Search Report dated Nov. 6, 2003 for EP application 03250103.3.
EPO Search Report dated Nov. 6, 2003 for EP application 03250109.0.
EPO Search Report dated Dec. 16, 2003 for EPO Appl. No. EP 01 30 9630.

* cited by examiner

STENT GRAFT WITH BRANCH LEG

CROSS-REFERENCE TO RELATED APPLICATIONS

This application is a continuation-in-part of U.S. application Ser. No. 09/714,080, filed on Nov. 16, 2000, now U.S. Pat. No. 6,656,215; U.S. application Ser. No. 09/714,093, filed on Nov. 16, 2000 now abandoned; U.S. application Ser. No. 09/714,078 filed on Nov. 16, 2000 now U.S. Pat. No. 6,626,938; and U.S. application Ser. No. 09/714,079, filed on Nov. 16, 2000 now U.S. Pat. No. 6,482,227.

BACKGROUND OF THE INVENTION

1. Field of the Invention

The present invention relates to devices and methods for repairing aneurysms, and more particularly, to percutaneously and/or intraluminally delivered devices and methods for repairing aneurysms, such as abdominal aortic aneurysms and thoracic aortic aneurysms.

2. Discussion of the Related Art

An aneurysm is an abnormal dilation of a layer or layers of an arterial wall, usually caused by a systemic collagen synthetic or structural defect. An abdominal aortic aneurysm is an aneurysm in the abdominal portion of the aorta, usually located in or near one or both of the two iliac arteries or near the renal arteries. The aneurysm often arises in the infrarenal portion of the diseased aorta, for example, below the kidneys. A thoracic aortic aneurysm is an aneurysm in the thoracic portion of the aorta. When left untreated, the aneurysm may rupture, usually causing rapid fatal hemorrhaging.

Aneurysms may be classified or typed by their position as well as by the number of aneurysms in a cluster. Typically, abdominal aortic aneurysms may be classified into five types. A Type I aneurysm is a single dilation located between the renal arteries and the iliac arteries. Typically, in a Type I aneurysm, the aorta is healthy between the renal arteries and the aneurysm and between the aneurysm and the iliac arteries.

A Type II A aneurysm is a single dilation located between the renal arteries and the iliac arteries. In a Type II A aneurysm, the aorta is healthy between the renal arteries and the aneurysm, but not healthy between the aneurysm and the iliac arteries. In other words, the dilation extends to the aortic bifurcation. A Type II B aneurysm comprises three dilations. One dilation is located between the renal arteries and the iliac arteries. Like a Type II A aneurysm, the aorta is healthy between the aneurysm and the renal arteries, but not healthy between the aneurysm and the iliac arteries. The other two dilations are located in the iliac arteries between the aortic bifurcation and the bifurcations between the external iliacs and the internal iliacs. The iliac arteries are healthy between the iliac bifurcation and the aneurysms. A Type II C aneurysm also comprises three dilations. However, in a Type II C aneurysm, the dilations in the iliac arteries extend to the iliac bifurcation.

A Type III aneurysm is a single dilation located between the renal arteries and the iliac arteries. In a Type III aneurysm, the aorta is not healthy between the renal arteries and the aneurysm. In other words, the dilation extends to the renal arteries.

A ruptured abdominal aortic aneurysm is presently the thirteenth leading cause of death in the United States. The routine management of abdominal aortic aneurysms has been surgical bypass, with the placement of a graft in the involved or dilated segment. Although resection with a synthetic graft via transperitoneal or retroperitoneal procedure has been the standard treatment, it is associated with significant risk. For example, complications include perioperative myocardial ischemia, renal failure, erectile impotence, intestinal ischemia, infection, lower limb ischemia, spinal cord injury with paralysis, aorta-enteric fistula, and death. Surgical treatment of abdominal aortic aneurysms is associated with an overall mortality rate of five percent in asymptomatic patients, sixteen to nineteen percent in symptomatic patients, and is as high as fifty percent in patients with ruptured abdominal aortic aneurysms.

Disadvantages associated with conventional surgery, in addition to the high mortality rate, include an extended recovery period associated with the large surgical incision and the opening of the abdominal cavity, difficulties in suturing the graft to the aorta, the loss of the existing thrombosis to support and reinforce the graft, the unsuitability of the surgery for many patients having abdominal aortic aneurysms, and the problems associated with performing the surgery on an emergency basis after the aneurysm has ruptured. Further, the typical recovery period is from one to two weeks in the hospital, and a convalescence period at home from two to three months or more, if complications ensue. Since many patients having abdominal aortic aneurysms have other chronic illnesses, such as heart, lung, liver and/or kidney disease, coupled with the fact that many of these patients are older, they are less than ideal candidates for surgery.

The occurrence of aneurysms is not confined to the abdominal region. While abdominal aortic aneurysms are generally the most common, aneurysms in other regions of the aorta or one of its branches are possible. For example, aneurysms may occur in the thoracic aorta. As is the case with abdominal aortic aneurysms, the widely accepted approach to treating an aneurysm in the thoracic aorta is surgical repair, involving replacing the aneurysmal segment with a prosthetic device. This surgery, as described above, is a major undertaking, with associated high risks and with significant mortality and morbidity.

Over the past five years, there has been a great deal of research directed at developing less invasive, endovascular, i.e. catheter directed, techniques for the treatment of aneurysms, specifically abdominal aortic aneurysms. This has been facilitated by the development of vascular stents, which can and have been used in conjunction with standard or thin-wall graft material in order to create a stent-graft or endograft. The potential advantages of less invasive treatments have included reduced surgical morbidity and mortality along with shorter hospital and intensive care unit stays.

Stent-grafts or endoprostheses are now FDA approved and commercially available. Their delivery procedure typically involves advanced angiographic techniques performed through vascular accesses gained via surgical cutdown of a remote artery, which may include the common femoral or brachial arteries. Over a guidewire, the appropriate size introducer will be placed. The catheter and guidewire are passed through the aneurysm. Through the introducer, the stent-graft will be advanced to the appropriate position. Typical deployment of the stent-graft device requires withdrawal of an outer sheath while maintaining the position of the stent-graft with an inner-stabilizing device. Most stent-grafts are self-expanding; however, an additional angioplasty procedure, e.g., balloon angioplasty, may be required to secure the position of the stent-graft. Following the placement of the stent-graft, standard angiographic views may be obtained.

Due to the large diameter of the above-described devices, typically greater than twenty French (3F=1 mm), arteriotomy closure typically requires open surgical repair. Some procedures may require additional surgical techniques, such as hypogastric artery embolization, vessel ligation, or surgical bypass, in order to adequately treat the aneurysm or to maintain flow to both lower extremities. Likewise, some procedures will require additional, advanced catheter directed techniques, such as angioplasty, stent placement, and embolization, in order to successfully exclude the aneurysm and efficiently manage leaks.

While the above-described endoprostheses represent a significant improvement over conventional surgical techniques, there is a need to improve the endoprostheses, their method of use and their applicability to varied biological conditions. Accordingly, in order to provide a safe and effective alternate means for treating aneurysms, including abdominal aortic aneurysms and thoracic aortic aneurysms, a number of difficulties associated with currently known endoprostheses and their delivery systems must be overcome. One concern with the use of endoprostheses is the prevention of endo-leaks and the disruption of the normal fluid dynamics of the vasculature. Devices using a technology should preferably be simple to position and reposition as necessary, should preferably provide an acute fluid tight seal, and should preferably be anchored to prevent migration without interfering with normal blood flow in both the aneurysmal vessel as well as branching vessels. In addition, devices using the technology should preferably be able to be anchored, sealed, and maintained in bifurcated vessels, tortuous vessels, highly angulated vessels, partially diseased vessels, calcified vessels, odd shaped vessels, short vessels, and long vessels. In order to accomplish this, the endoprostheses should preferably be extendable and re-configurable while maintaining acute and long-term fluid tight seals and anchoring positions.

The endoprostheses should also preferably be able to be delivered percutaneously utilizing catheters, guidewires and other devices that substantially eliminate the need for open surgical intervention. Accordingly, the diameter of the endoprostheses in the catheter is an important factor. This is especially true for aneurysms in the larger vessels, such as the thoracic aorta.

SUMMARY OF THE INVENTION

The stent graft with branch leg of the present invention provides a means for overcoming the problems associated with extending by-pass grafts into bifurcated sections of arteries as briefly described above.

The present invention is directed to a system including at least one prosthesis for repair or replacement of a mammalian body part or condition. The typical system includes a first prosthesis for sealing the system within a predetermined portion of an artery; at least one second prosthesis engaged to the first prosthesis, the second prosthesis providing a fluid flow path through the system or a portion of the system; and a third or extension prosthesis for extending a fluid flow path through the system or a portion of the system. In some embodiments of the invention, the second prosthesis is sealingly and/or matingly engaged with the first prosthesis. In some embodiments of the invention, the extension prosthesis extends the fluid flow path formed by the second prosthesis. In some embodiments of the invention, the extension prosthesis is sealingly and/or matingly engaged with the second prosthesis.

A typical first prosthesis includes a support or stent structure, and a foam or gasket material supported by the stent, the stent and gasket material being configured to seal the system within an artery. A typical first prosthesis also includes one or more structures or elements for engaging the second prosthesis. In preferred embodiments of the invention, these elements or structures sealing and/or matingly engage the second prosthesis. The stent is typically a synthetic or natural matrix for supporting the gasket material. In some exemplary embodiments of the stent, the stent is a hollow, substantially cylindrical, and preferably radially expandable matrix having a lumen and two open ends. The typical gasket material is a synthetic or natural fabric, tissue, foam, or the like. In preferred embodiments of the invention, the gasket material covers at least a portion of the lumen, even more preferably, the proximal end of the lumen.

A system according to the present invention is intended for repairing or bypassing an aneurysm, preferably an aortic aneurysm. The system may also be used to direct fluid flow from one portion of a fluid pathway to another. The typical system according to the invention may include multiple system components, e.g., more than one prosthesis, with the first prosthesis typically positioned upstream of an aneurysm. In preferred embodiments of the invention, the first prosthesis includes one or more structures that seal the system, and position the system components in their proper position. The first prosthesis also preferably includes gasket material configured and adapted to facilitate delivery of other system components, to receive and/or position other system components, and/or to establish at least one fluid flow path through the system.

For example, a system may include a first prosthesis configured to be positioned in an artery upstream of an aneurysm, and a second prosthesis that matingly engages the first prosthesis and provides a fluid flow path that bypasses the aneurysm. As will be evident from the description below, the system may include a variety of other components all adapted to communicate with another component in the system, with a particular assembly of components designed to establish one or more fluid flow paths that bypass a pre-determined location, e.g., a location that includes an aneurysm and/or an arterial junction. For example, the system may include a third prosthesis that matingly engages the second prosthesis and provides a fluid flow path through an artery disposed downstream from the first aneurysm wherein the fluid flow path bypasses an aneurysm disposed in the downstream artery.

The accompanying figures show illustrative embodiments of the invention from which these and other of the objectives, novel features and advantages will be readily apparent.

BRIEF DESCRIPTION OF THE DRAWINGS

The foregoing and other aspects of the present invention will best be appreciated with reference to the detailed description of the invention in conjunction with the accompanying drawings. Throughout the figures and the description below, like numerals indicate the same element.

DETAILED DESCRIPTION OF THE PREFERRED EMBODIMENTS

Figure 1:
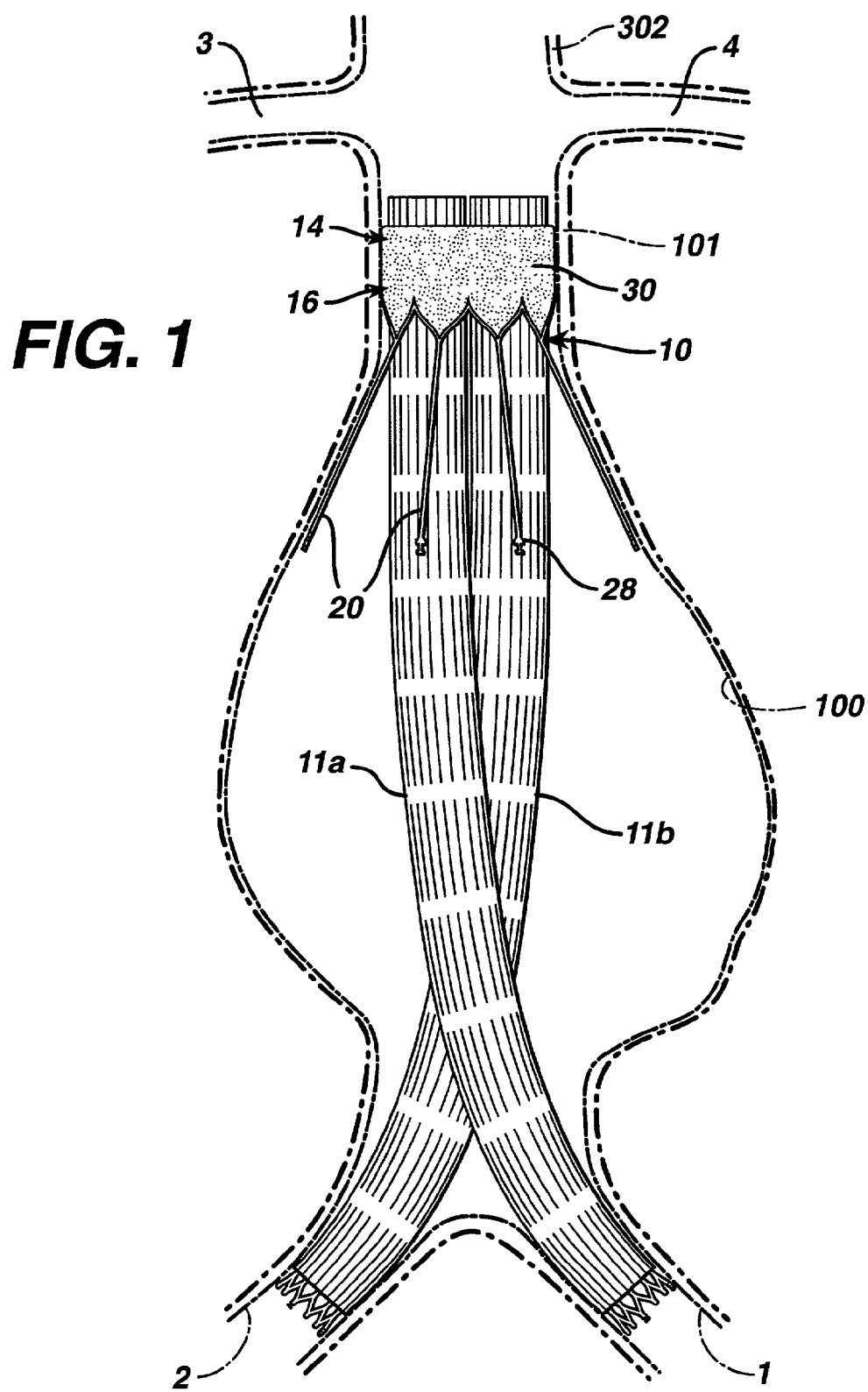
FIG. 1 is an elevation view of a fully deployed aortic repair system made in accordance with the present invention.

The apparatuses, systems, methods, and kits of the present invention may be used in the treatment of aortic aneurysms, preferably an abdominal aortic aneurysm, among other uses noted below. More preferably, the present invention may be used to treat Schumacher Type IIC abdominal aortic aneurysms and Type III abdominal aortic aneurysms. A better understanding of the present device and its use in treating aortic aneurysms will be achieved by reading the following description in conjunction with the above-incorporated references.

The present invention embodies a prosthesis for repairing or bypassing an aneurysm, the prosthesis comprising a graft material engaging a stent, the stent comprising a first matrix of interconnected struts configured to engage an upstream section of an artery, and a second matrix of interconnected struts configured to engage a downstream section of the artery, the stent including an intermediate portion comprising a plurality of struts extending away from said stent. A portion of the first matrix and/or the second matrix preferably includes graft material engaging the respective matrix and the plurality of struts. The struts together with the graft material preferably form a branch leg that forms a conduit for fluid flow separate from the second matrix.

An exemplary embodiment of the present invention includes a first prosthesis for repairing or bypassing an aneurysm, the first prosthesis comprising a gasket material engaging a stent, the stent comprising a first matrix of interconnected struts configured to engage a section of an artery upstream of an aneurysm, the graft material being configured to receive at least one second prosthesis, the second prosthesis being configured for establishing a fluid flow channel through the aneurysm. At least one-third prosthesis may be coupled to the second prosthesis to establish a fluid flow channel through a downstream artery, e.g., a common iliac artery. The third prosthesis preferably includes a main leg and a branch leg, the main leg being configured to create a fluid flow path in one of the internal and external iliac arteries and the branch leg being configured to create a fluid flow path in the other of the internal and external iliac arteries.

An exemplary embodiment of the present invention includes a stent gasket or first prosthesis for repairing or bypassing an aneurysm, the first prosthesis comprising a graft material engaging a stent, the stent comprising a first matrix of interconnected struts configured to engage a section of an artery upstream of an aneurysm, the graft material being configured to receive at least one second prosthesis, the second prosthesis being configured for establishing a fluid flow channel through the aneurysm, the second prosthesis further including a branch leg configured for establishing a fluid flow channel into a cross artery.

The present invention also includes an anchor, stent, or prosthesis as described above, wherein an intermediate portion of the anchor, stent, or prosthesis includes an aperture in the stent matrix having a plurality of struts disposed about a perimeter of the aperture and extending away from the intermediate portion. In preferred embodiments, the graft material not only engages the stent matrix but also includes a portion covering the struts to form a branch leg.

The present invention is also directed to a system for repairing or bypassing an aneurysm, said system being variously configured and/or assembled using components described in more detail below. Typical systems according to this aspect of the invention may include one or more first prostheses or a sealing component, one or more second prostheses or a fluid flow component, and, optionally, one or more component receptacles, assemblies, or connectors for matingly engaging one component with another. Preferred embodiments of a system of the present invention include a sealing component matingly engaged to two fluid flow path components.

A system of the present invention may comprise various components, elements, and/or prostheses, the combination of which preferably provide four functions:

1) an anchor positioned upstream of a cross artery, providing an anchoring function for the system; the typical anchor comprises an uncovered stent portion configured to exert a radial force against the wall of the artery;

2) a trans- or para-region that spans the cross artery, providing a flexible and open connection between the upstream portion of the system and the downstream portion; the typical trans-region comprises a highly flexible uncovered stent portion or bridge section;

3) a fluid tight seal, providing a sealing function that prevents fluid leakage outside the system; the typical sealing element or prosthesis is positioned downstream of the cross artery, and includes a sealing diaphragm configured to seat another element or prosthesis that defines a fluid flow path; and 4) a delivery system guide, providing a guiding function for the various elements of the delivery system; the typical guide is a flared portion of the downstream end of the system, said flared portion providing proper orientation or channeling of the catheter elements used to deliver the various components of the system.

Any of the prostheses or stents described above may form a component or portion of a system or kit for repairing or bypassing an aneurysm.

Any of the prostheses, stents, systems, or kits described above may be incorporated in a method for treating an aneurysm. In preferred embodiments of the invention, the prostheses, stents, systems, or kits are used to treat an aortic aneurysm, even more preferably, an abdominal aortic aneurysm.

A method of the present invention includes delivering a prosthesis in a first branch of a bifurcated artery to create a first fluid flow path, the prosthesis including a branch leg, deploying the branch leg upstream from the artery bifurcation and engaging a second prosthesis with the branch leg to create a fluid flow path in the second branch of the bifurcated artery.

A method of the present invention comprises delivering and deploying a first prosthesis upstream of an aneurysm, the first prosthesis being adapted to receive at least one second prosthesis, the second prosthesis including a branch leg, and positioning the branch leg in an artery upstream of the aneurysm; and positioning an upstream end of at least one second prosthesis in an upstream end of the first prosthesis. In some embodiments of the invention, the method may further include positioning a downstream end of the second prosthesis in an artery downstream of the aneurysm.

Exemplary prostheses and methods of the present invention may be configured to repair an abdominal aortic aneurysm. In these embodiments of the invention, the first prosthesis may be positioned in an infra-renal or supra-renal portion of the abdominal aorta, the second prosthesis may extend into one of the iliac arteries, and the branch leg of the second prosthesis may extend into one of the renal arteries.

The present invention is also directed to a kit that includes one or more of the following: a sterile or sterilizable enclosure; a first prosthesis; a first prosthesis in an individual sterile enclosure; a second prosthesis; a second prosthesis in an individual sterile enclosure; at least one suture; at least one staple; a collar or catheter tip assembly configured to engage and deliver a first prosthesis, a second prosthesis; and at least one marker configured for placement on a first prosthesis, a second prosthesis, a third prosthesis, and/or portions thereof. The kit may also include a third prosthesis; a third prosthesis in an individual sterile enclosure where the collar or catheter tip may be used to deliver the third prosthesis.

The present invention also includes a kit comprising a prosthesis according to the invention, preferably in a sterile or sterilizable enclosure.

Embodiments of the invention may further include one or more second and/or third prostheses configured to matingly engage a first prosthesis, the second and/or third bypass prosthesis comprising a graft material engaging a stent, the stent comprising a hollow matrix comprising a series of interconnected struts, the matrix being moveable from a first closed position to a second open position; the stent having at least one attachment structure or connector for matingly engaging at least one second complementary structure on the first prosthesis. In some embodiments of the invention, the prosthesis further comprises at least one marker. In preferred embodiments of the invention, the marker or markers are positioned on or formed as part of the stent.

Other embodiments of the invention will be evident from the description provided below.

Definitions

As used herein, aortic aneurysm refers to any failure of a conduit, such as an aortic wall, typically characterized by an undesirable dilation of a portion of the artery, vessel malformation, or an occlusion. The system and structures of the present invention may be used to treat, repair, replace, or bypass any blood vessel (e.g., artery, vein, capillary); any fluid carrying vessel (e.g., lymphatic vessels); any organ or portion thereof that includes a blood or fluid vessel; or any junction between blood vessels, between fluid vessels, and between organs and blood vessels. An exemplary use of a system and method of the present invention is to repair an aortic aneurysm, and the use of such term is not intended to limit the use of the structures or systems of the present invention to repair or replace other conduit failures. The prosthesis of the present invention may also be utilized in the thoracic aorta, and can be used to repair thoracic aneurysms or thoracic dissecting aneurysms. Accordingly, use of the term "aortic aneurysm" is intended to relate to and include other aneurysms, including but not limited to both abdominal aortic aneurysms and thoracic aneurysms.

In preferred embodiments of the invention, the system and structures are used to treat, repair, replace, or bypass an abdominal aortic aneurysm, specifically, Schumacher Type III and Type IIC aneurysms.

As used herein fluid pathway refers to any in vivo structure through which a biological fluid passes. A preferred fluid pathway is an artery. Fluid pathways include, but are not limited to channels formed by an artery, a vein, a capillary, lymph nodes and channels, and arteries, veins, and capillaries within an organ or organelle.

As used herein fluid or biological fluid refers to any fluid produced by an animal including a human. Exemplary biological fluids include but are not limited to blood, oxygenated blood, de-oxygenated blood, gastric fluids, amniotic fluid, cerebro spinal fluid, and lymph. The preferred fluid is blood or oxygenated blood.

As used herein, conduit typically refers to any structure used to convey a biological fluid. The conduit may be formed of natural or synthetic materials, or combinations thereof. Exemplary conduits include but are not limited to an artery, a vein, a capillary, lymph nodes and channels, and arteries, veins, capillaries within an organ or organelle, and a prosthesis or system according to the invention.

As used herein, "biofusion" is a word coined by assignee referring to the ability cells, proteins, fibrin, and other biological molecules to incorporate into the pore structure of a material, such as a foam or gasket material, or a graft material. It is believed that this feature promotes a long-term stable biological interface that cannot be separated approximately six weeks after implantation.

The biofusion effect has many advantages. It has the potential to obviate late endo-leakage by preventing areas of non-organized clot from being displaced or recanalized. It is also believed that biofusion creates a connective tissue collar around the prosthesis that may prevent the aortic neck from dilating over time. Restricting neck dilation avoids leakage pathways and implant migration that can be caused by an insufficient fit with the aorta.

As used herein, adapted for communication, communicating, or similar terms refer to any means, structures, or methods for establishing operational association between two elements of the system. Similarly, engaging, adapted to engage, or similar terms refer to means, structures, or methods for contacting a first component, structure, or portion thereof with a second component, structure, or portion thereof. Exemplary structures are shown in the Figures. Typically, all of these terms and phrases refer to at least one structure in or on a first component configured to engage a complementary structure in or on a second component, and the use of these inter-engaging features to link a first prosthesis or component with a second prosthesis or component. The engagement or communication may be matingly (e.g., permanent) and/or releasably (e.g., temporary). In preferred embodiments of the invention, communication or engagement may be fluid tight, substantially fluid tight, or fluid tight to an extent so as to not substantially compromise the intended function of the structure.

For example, a connector may be adapted to receive or connect to a complementary connector on another prosthesis. As used herein, connector refers to any structure used to form a joint or to join itself to another component or portion thereof. These connectors or connections establish a fluid flow path through various elements of the apparatus, assembly, or system. In a preferred embodiment of the invention, the system is intended to establish at least one fluid flow path through a vessel, conduit, organ, or portions thereof. Typical connections include but are not limited to mating connections, such as Luer-type, screw-type, friction-type, or connectors that are bonded together.

As used herein, distal is used in accordance with its ordinary dictionary definition, e.g., referring to a position farthest from the beginning; in human anatomy, this term is commonly equivalent to caudal or inferior. Proximal is used in accordance with its ordinary dictionary definition, e.g., referring to a position nearest the beginning; in human anatomy, this term is commonly equivalent to cranial or superior. The terms distal and proximal are intended to convey opposite ends or portions of a device, channel, element, or structure. In relation to a fluid flow path, distal will typically refer to a downstream location in the fluid flow path, and proximal will typically refer to an upstream location, unless otherwise specifically noted. Anatomically, distal generally refers to "away from the heart" and proximal generally refers to "toward the heart."

A system for treating an aortic aneurysm according to the present invention typically includes a first prosthesis and at least one second prosthesis. In preferred embodiments of the invention, the components of the system are delivered percutaneously and/or intraluminally to the site of the aneurysm using a catheter or the like. One skilled in the art will therefore recognize that it is beneficial to deliver the components of the system in an unexpanded or first position, and to deploy the component in its functional location by expanding the component into an expanded or second position. A typical second prosthesis forms a fluid flow channel that bypasses the aneurysm.

Figure 10:
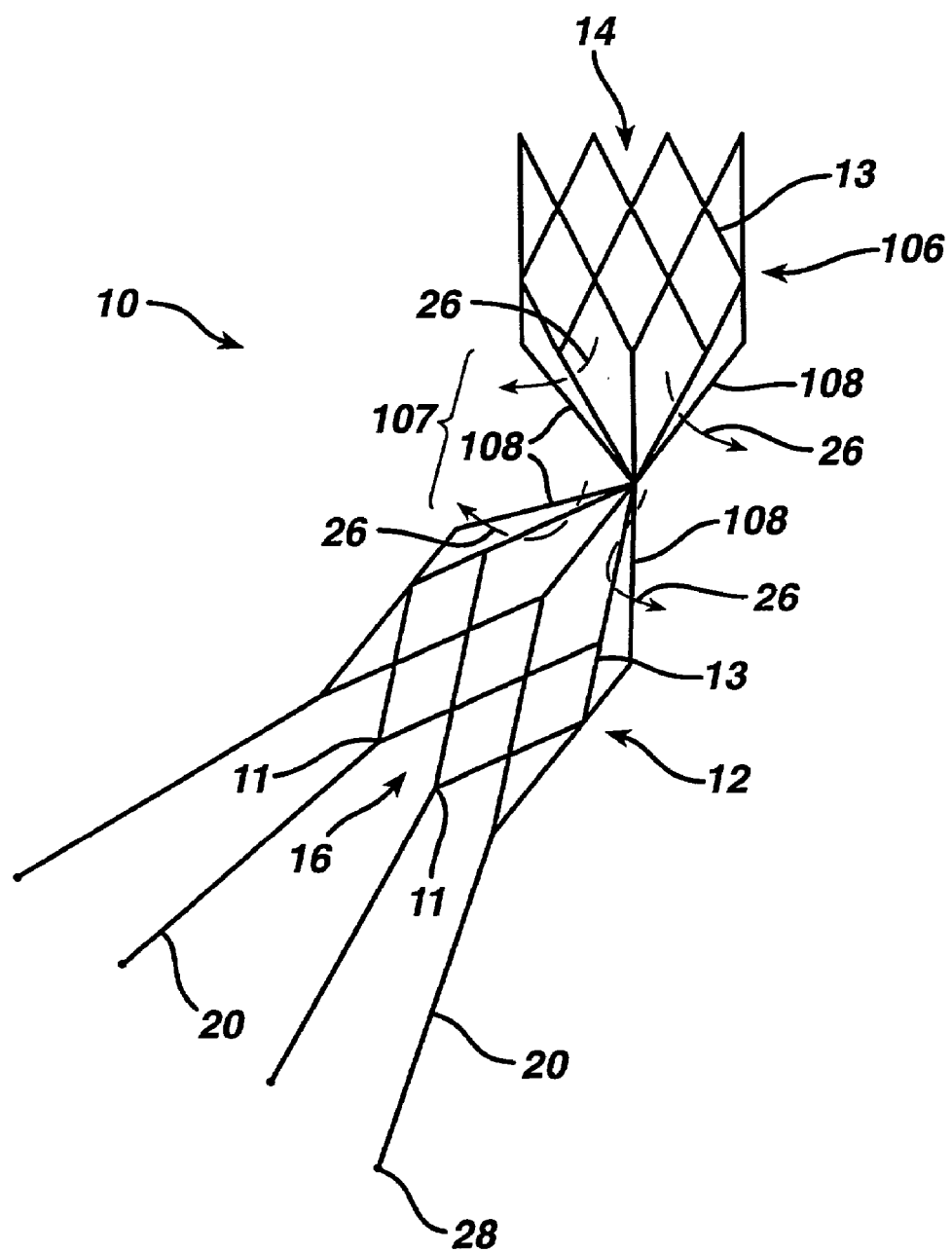
FIG. 10 is a side elevation of an embodiment of a stent of the present invention having an angled upstream extension anchor.

Jointed stent, as used herein, refers to any stent structure or configuration that permits one section of the stent to be angled in relation to another section. The angled configuration can be fixed or may be fixed or moveable, flexible or non-flexible, preferably to accommodate the angle of the artery in which the prosthesis is placed. An exemplary embodiment is shown in FIG. 10. Although the angle may be any angle, the preferred stent of the present invention has greater than about a forty-five degree angle between the two sections. A flexible stent structure, wherein the flexibility is derived from the bridge and/or strut configuration itself, may provide sufficient flexibility and/or articulation to accommodate extreme angulations in an artery's shape. These various flexible stent structures are also included in the meaning of jointed stent.

Each of the components of the system will now be described in more detail. Any references to the Figures will be used to illustrate one or more embodiments of the invention, without intending to limit the invention thereby.

System

Figure 8:
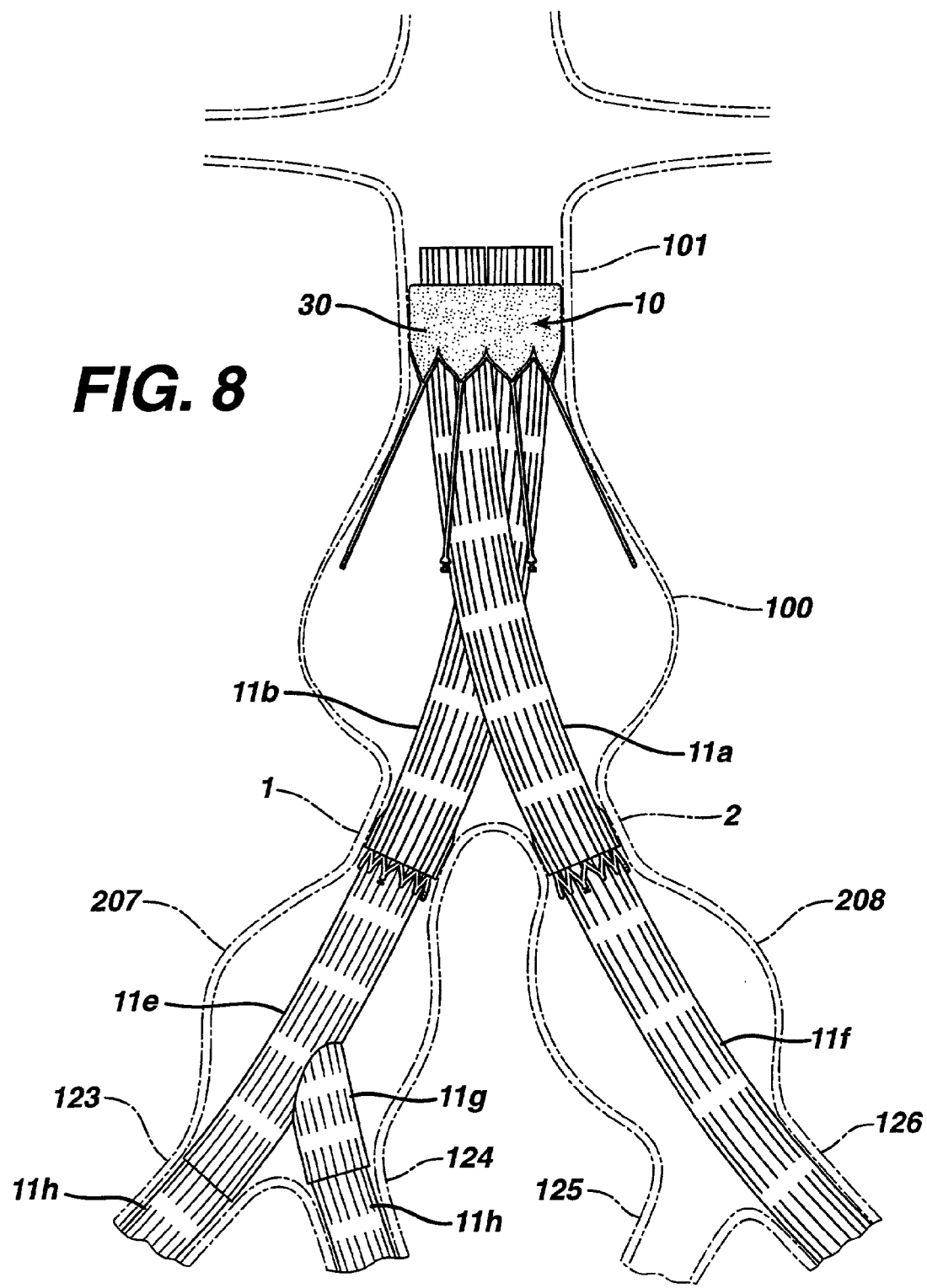
FIG. 8 is an elevation view of an embodiment of a fully deployed aortic repair system of the present invention configured with a prosthesis disposed in the common iliac artery to bypass a common iliac aneurysm while maintaining adequate fluid flow in internal and external iliac arteries.
Figure 13:
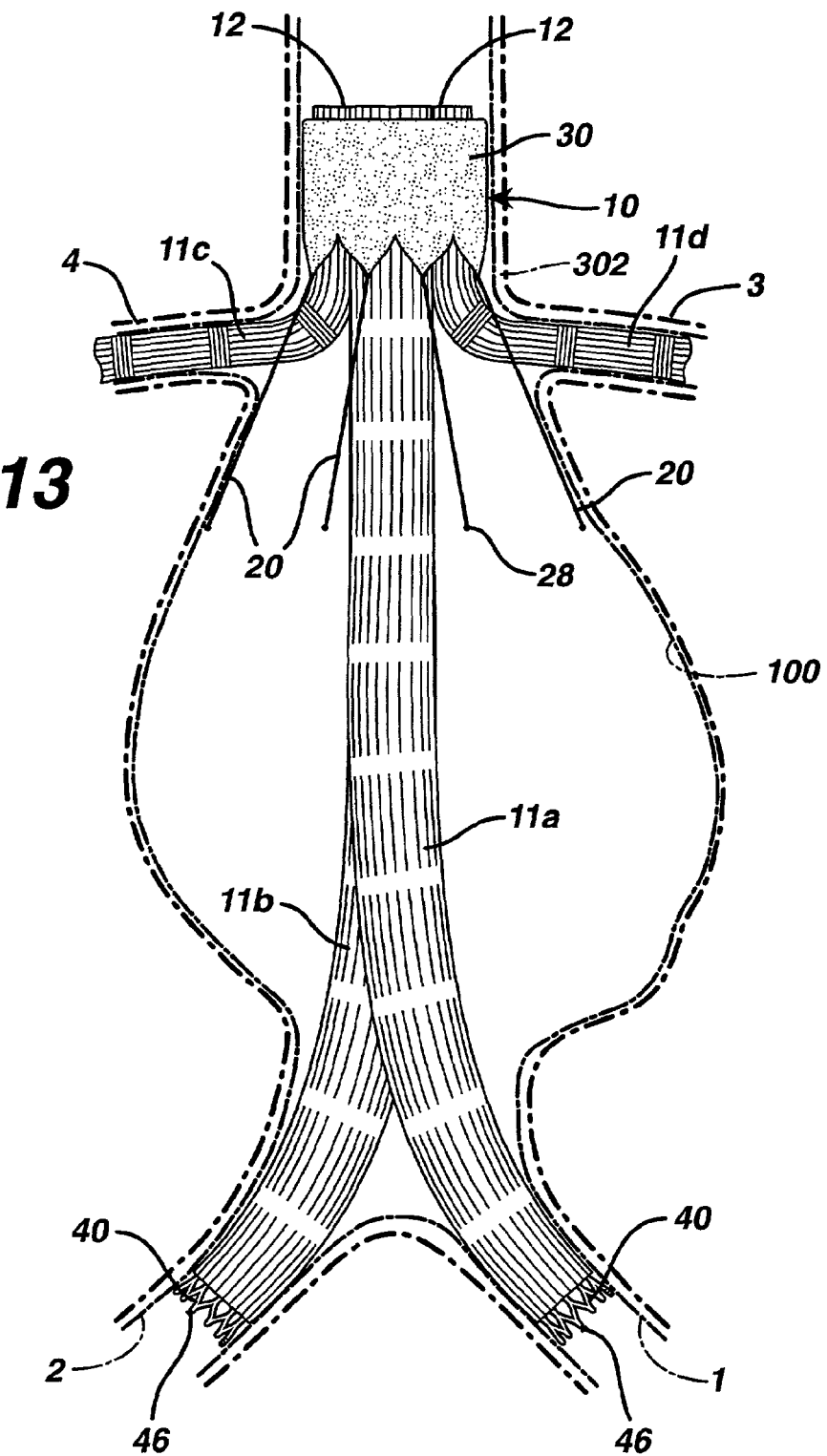
FIG. 13 shows another embodiment of the invention.

A system according to the present invention may include one or more prostheses. Exemplary systems are shown in FIGS. 1, 8 and 13. The system includes a first prosthesis 10, for example, a suprarenal stent gasket (FIG. 13) or an infrarenal stent gasket (FIGS. 1 and 8), and at least one second prosthesis, preferably two second prostheses 11*a* and 11*b*, which, in combination, bypass an aneurysm 100. In preferred embodiments of the invention, an upstream portion of the system may be positioned in a section 101 of an artery upstream of the aneurysm 100, and a downstream portion of the system may be positioned in a downstream section of the artery or a different artery. In some embodiments, the second prostheses 11*a* and 11*b* may also each include additional bypass prostheses 11*c* and 11*d* (FIG. 13), respectively which may be configured to provide a fluid flow channel into an artery or the like upstream of the aneurysm, e.g., a renal artery 3 or 4.

As shown most clearly in FIG. 8, the system of the present invention is particularly suited for use when the aneurysmal disease has spread to one or both of iliac arteries 1 and 2, for example, a Type IIC aneurysm. Under these and other circumstances, it may be desirable to employ extension prostheses to bypass aneurysms 207 and 208 present in the iliac arteries.

As shown in FIG. 13, it may also be beneficial to provide a system wherein additional bypass prostheses 11*c, d* may be utilized as branch legs for channeling fluid flow into a cross or second artery 3 or 4. A third prosthesis or extension cuff may be coupled to the additional bypass prostheses 11*c, d*, if desired, to provide deeper access into the cross or second artery 3 or 4.

A prosthesis of the present invention includes a support, stent, or lattice of interconnected struts defining an interior space having an open proximal/upstream end and an open distal/downstream end. The lattice also defines an interior surface and an exterior surface. The interior and/or exterior surfaces of the lattice, or a portion of the lattice, may be covered by or support at least covering material, such as a foam or graft material.

As noted in more detail below in relation to specific system components, some prostheses of the present invention may be configured to seal and/or anchor the system in place, and/or to receive and position other prostheses. Typically these prostheses do not themselves define a fluid flow path. Other prostheses may be configured to define at least one fluid flow path. Typically, these prostheses define a channel or the like through which fluid, such as blood, flows. This channel or fluid flow path typically begins upstream of, or in an upstream portion of, a component of the system. In some embodiments of the invention, the fluid flow path bypasses the aneurysm.

Figure 5:
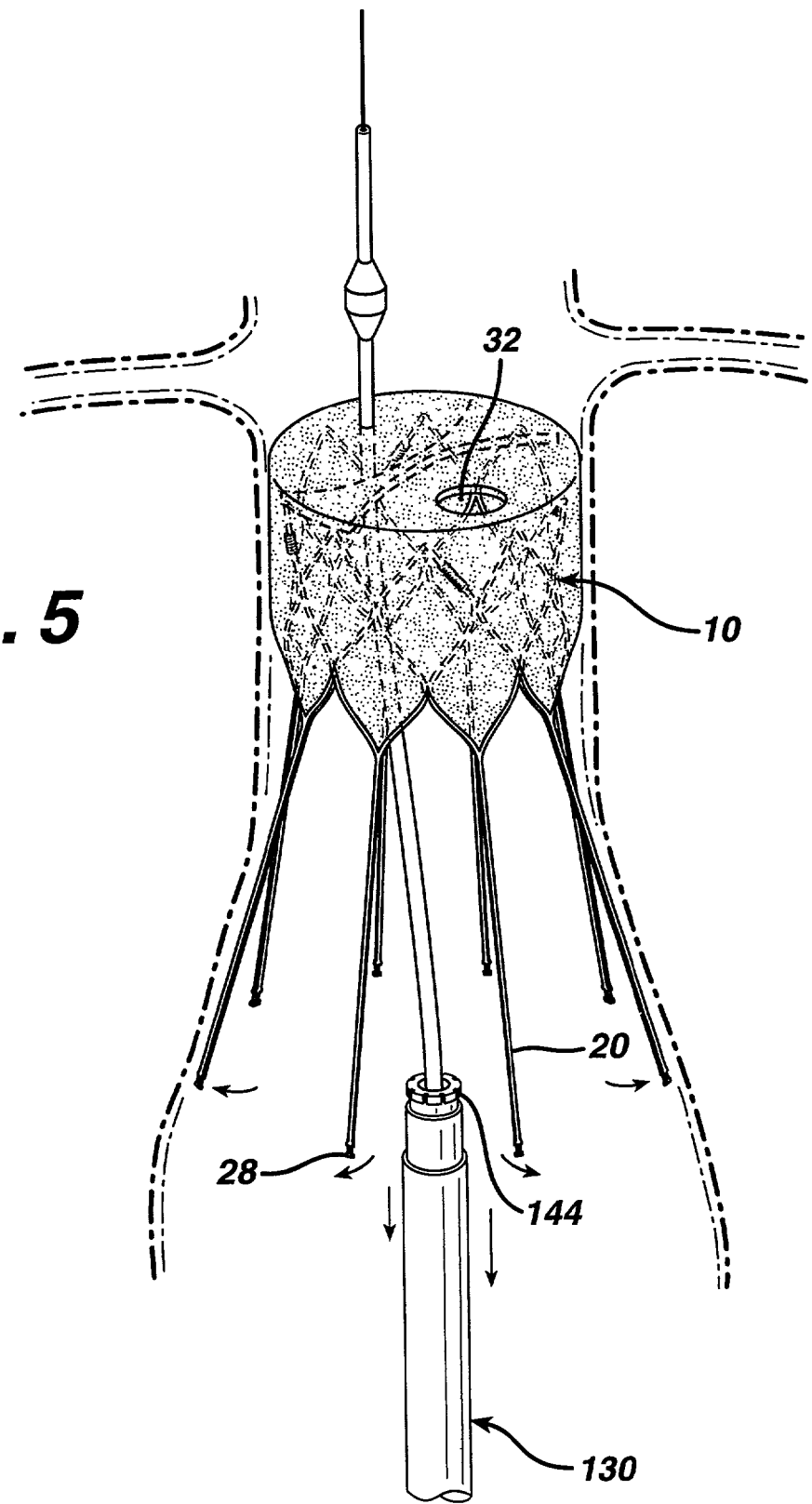
FIG. 5 is an elevation view of a fully deployed first prosthesis made in accordance with the present invention and an exemplary delivery system.
Figure 6:
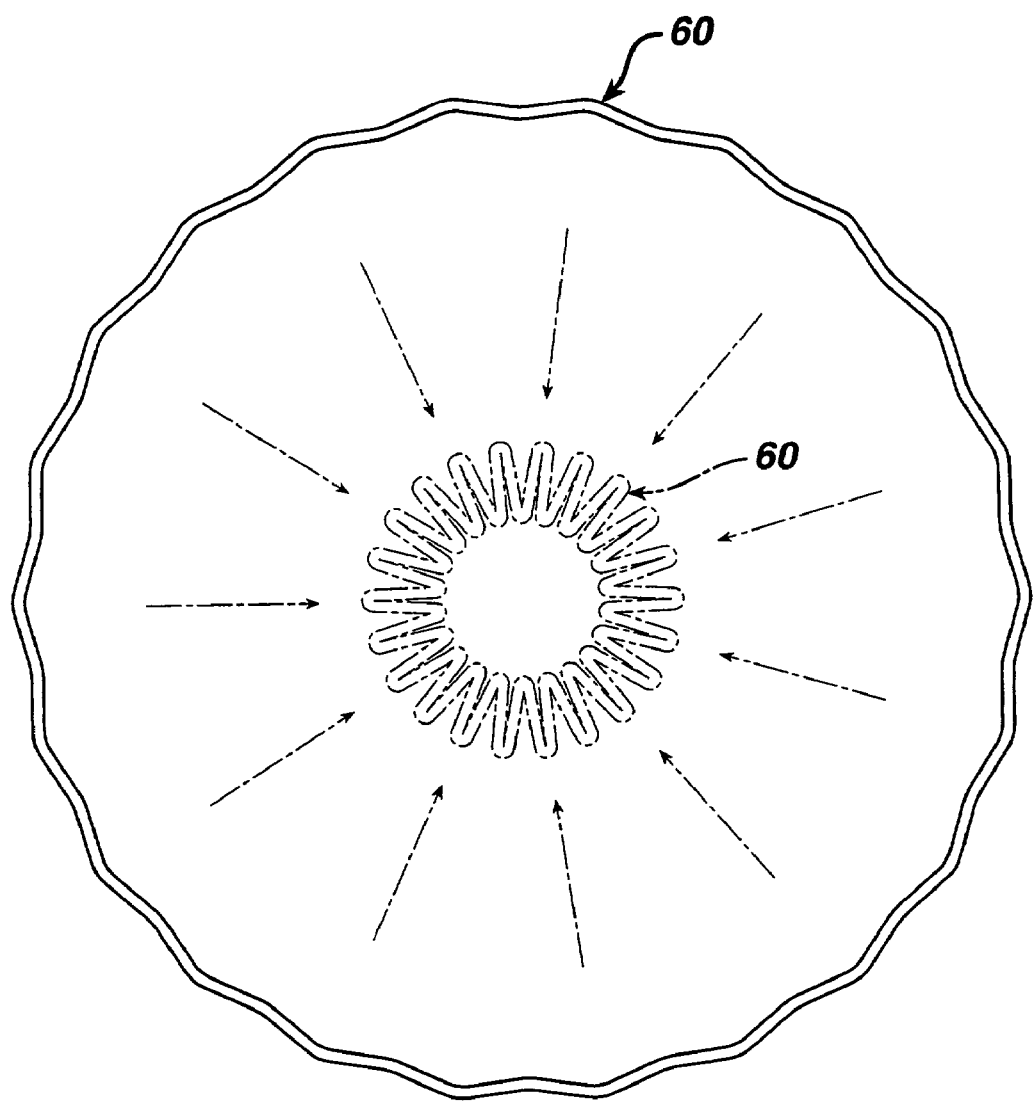
FIG. 6 is an end view of the graft material illustrating the graft material in its closed configuration and its fully open configuration.
Figure 7:
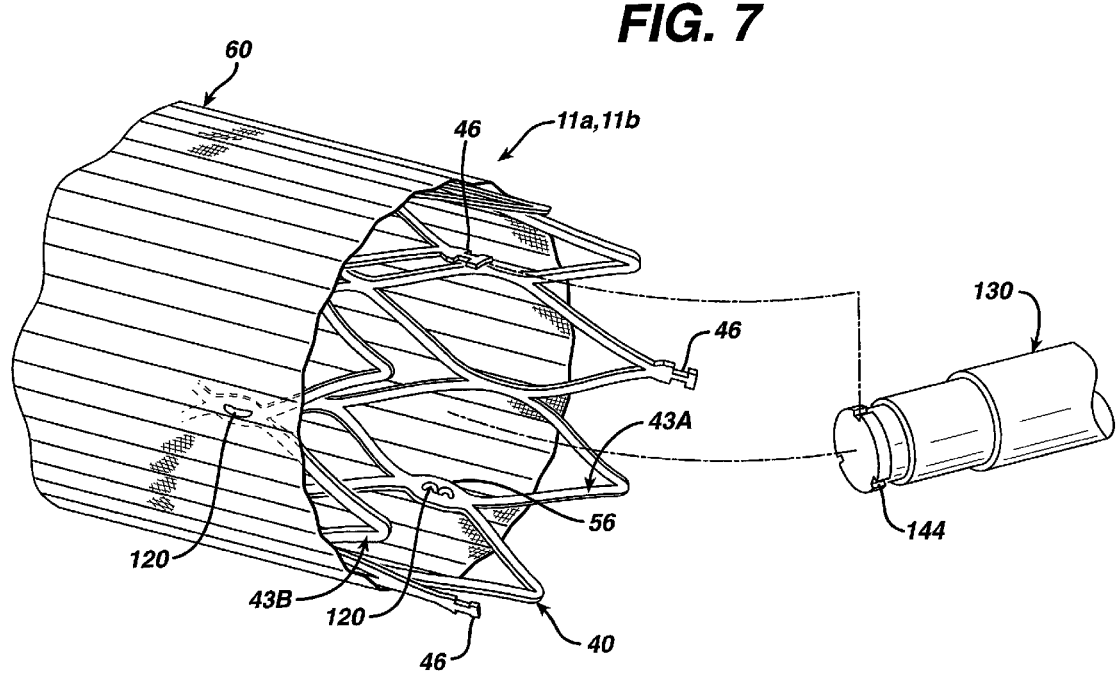
FIG. 7 is a partial, exploded perspective view of the downstream end of a second prosthesis of the present invention illustrating an anchoring and delivery system according to the invention.

In preferred embodiments of the invention, a prosthesis is moveable between an expanded or inflated position and an unexpanded or deflated position, and any position therebetween. An exemplary embodiment showing the graft in its expanded and unexpanded positions is illustrated in FIG. 6 and is intended to generally illustrate a stent or stent graft in its expanded or unexpanded position. In some embodiments of the invention, it may be desirable to provide a prosthesis that moves only from fully collapsed to fully expanded. In other embodiments of the invention, it may be desirable to expand the prosthesis, then collapse or partially collapse the prosthesis. Such capability is beneficial to the interventionist to properly position or re-position the prosthesis. In accordance with the present invention, the prosthesis may be self-expanding, or may be expandable using an inflatable device, such as a balloon or the like. Even further in accordance with the present invention, there is provided a delivery apparatus for a self-expanding prosthesis as shown in FIGS. 5 and 7. A more detailed description is given below.

Exemplary embodiments of a system for treating an abdominal aortic aneurysm according to the present invention are shown in FIGS. 1, 8 and 13. For the purpose of this embodiment, the system is deployed in the infrarenal neck 101 of the abdominal aorta, upstream of where the artery splits into left and right common iliac arteries. FIG. 1 shows stent gasket 10 positioned in the infrarenal neck 101; two prostheses, 11a and 11b, the upstream ends of which matingly engage an upstream portion of the stent gasket 10, and the downstream ends of which extend into a common iliac artery 1 or 2. As illustrated, the body of the prosthesis forms a conduit or fluid flow path that passes through the location of the aneurysm 100. In preferred embodiments of the invention, the components of the system define a fluid flow path that bypasses the section of the artery where the aneurysm is located.

A system in accordance with a preferred embodiment of the invention is depicted in FIG. 8. Stent gasket 10 is positioned in the infrarenal neck 101 engaged with two second prostheses, 11a and 11b, the upstream ends of which matingly engage an upstream portion of the stent gasket 10 and the downstream ends of which extend into a common iliac artery located downstream from the aneurysm, e.g. iliac arteries 1 or 2. As illustrated, the body of the prosthesis forms a conduit or fluid flow path that passes through the location of the aneurysm 100. In addition, in accordance with the invention a third prosthesis or extension prosthesis is coupled to at least one of prostheses 11a and 11b. More particularly, an upstream end of the third prosthesis may be coupled to a downstream end of one of the second prostheses 11a and 11b. Depending upon the condition of the arteries, each of second prostheses 11a and 11b may be matingly engaged with respective third prostheses 11e and 11f. As shown, the bodies of respective third prostheses 11e and 11f form conduits or fluid flow paths that pass through the location of aneurysms 207 and 208, respectively. At least one, and preferably both, of the third prostheses 11e and 11f includes a branch leg 11g that extends into one of the exterior and interior iliac arteries while the prosthesis extends into the other of the interior and exterior iliac artery to facilitate blood flow through the aneurysm to the internal and external iliac arteries. Branch leg 11g is defined by an aperture disposed in third prosthesis 11e having a plurality of struts extending radially, preferably substantially perpendicularly to the main stent axis, from the perimeter of the aperture and surrounding the aperture (see FIG. 4a). The struts are covered with graft material to form branch leg 11g. An extension cuff 11h may be coupled to branch leg 11g to provide deeper access into external iliac 123. This will improve sealing against endoleakage and create greater migration resistance at the junction of branch leg 11g and extension cuff 11h than if extension cuff 11h were inserted directly into the aperture e.g., if branch leg 11g did not exist and extension cuff 11h were inserted into an aperture in the third prosthesis 11e.

FIG. 13 shows a preferred embodiment in which stent gasket 10 is positioned in the supra-renal portion of abdominal aorta 302. In this exemplary embodiment, the upstream ends of the two prostheses, 11a and 11b, matingly engage an upstream portion of the stent gasket 10, and the downstream ends extend into a common iliac artery 1 or 2, bypassing aneurysm 100. Each of prostheses 11a and 11b are provided with additional second prostheses, 11c and 11d, the upstream ends of which are preferably mated with prostheses 11a and 11b and the downstream ends of which extend into a renal artery 3 or 4. As illustrated, the body of the prosthesis 11a and 11b forms a conduit or fluid flow path that passes through the location of the aneurysm 100; and the body of each additional second prosthesis, 11c and 11d, forms a conduit or fluid flow path that passes into an artery upstream of the aneurysm. In preferred embodiments of the invention, the components of the system define a fluid flow path that bypasses the section of the artery where the aneurysm is located.

These and other features of the prosthetic devices and systems of the present invention will be described in more detail below.

First Prosthesis or Sealing Prosthesis

The first prosthesis includes a support matrix or stent that supports a sealing material or foam, at least a portion of which is positioned across a biological fluid flow path, e.g., across a blood flow path. In preferred embodiments of the invention, the first prosthesis, the stent, and the sealing material are radially expandable, and define a hollow space between a proximal portion of the prosthesis and a distal portion of the prosthesis. The first prosthesis may also include one or more structures for positioning and anchoring the prosthesis in the artery, and one or more structures for engaging and fixing at least one second prosthesis in place, e.g., a bypass prosthesis.

The support matrix or stent of the first prosthesis may be formed of a wide variety of materials, may be configured in a wide variety of shapes, and their shapes and uses are well known in the art. Exemplary prior art stents are disclosed in U.S. Pat. No. 4,733,665 (Palmaz); U.S. Pat. No. 4,739,762 (Palmaz); and U.S. Pat. No. 4,776,337 (Palmaz), each of the foregoing patents being incorporated herein by reference.

In preferred embodiments of the invention, the stent of the first prosthesis is a collapsible, flexible, and self-expanding lattice or matrix formed from a metal or metal alloy, such as Nitinol or stainless steel. Structures formed from stainless steel may be made self-expanding by configuring the stainless steel in a predetermined manner, for example, by twisting it into a braided configuration. More preferably, the stent is a tubular frame that supports a sealing material. The term tubular, as used herein, refers to any shape having a sidewall or sidewalls defining a hollow space or lumen extending therebetween; the shape may be generally cylindrical, elliptic, oval, rectangular, triangular in cross-section or any other shape. Furthermore, the shape may change or be deformable as a consequence of various forces that may press against the stent or prosthesis.

The sealing material or gasket member supported by the stent may be formed of a wide variety of materials, may be configured in a wide variety of shapes, and their shapes and uses are well known in the art. Exemplary materials for use with this aspect of the invention are disclosed in U.S. Pat. No. 4,739,762 (Palmaz) and U.S. Pat. No. 4,776,337 (Palmaz), both incorporated herein by reference.

The sealing material or gasket member may comprise any suitable material. Exemplary materials are composed of a biodurable and biocompatible material, including but are not limited to, open cell foam materials and closed cell foam materials. Exemplary materials include polyurethane, polyethylene, polytetrafluroethylene; and other various polymer materials, preferably woven or knitted, that provide a flexible structure, such as Dacron. Highly compressible foams are particularly preferred, preferably to keep the crimped profile low for better delivery. The sealing material or foam is preferably substantially impervious to blood when in a compressed state.

The sealing material may cover one or more surfaces of the stent i.e., can be located along an interior or exterior wall, or both, and preferably extends across the proximal end or a proximal portion of the stent. The sealing material helps impede any blood trying to flow around the first prosthesis, e.g., between the first prosthesis and the arterial wall, and around one or more bypass prostheses after they have been deployed within the lumen of the first prosthesis (described in more detail below).

In preferred embodiments of the invention, the sealing material stretches or covers a portion of the proximal end of the stent and along at least a portion of the outside wall of the stent.

In some embodiments of the invention, it may be desirable for the portion of the sealing material covering the proximal portion of the stent to include one or more holes, apertures, points, slits, sleeves, flaps, weakened spots, guides, or the like for positioning a guidewire, for positioning a system component, such as a second prosthesis, and/or for engaging, preferably matingly engaging, one or more system components, such as a second prosthesis. For example, a sealing material configured as a cover or the like, and having a hole, may partially occlude the stent lumen.

These openings may be variously configured, primarily to conform to its use. These structures promote proper side by side placement of one or more, preferably multiple, prostheses within the first prosthesis, and, in some embodiments of the invention, the sealing material may be configured or adapted to assist in maintaining a certain shape of the fully deployed system or component. Further, these openings may exist prior to deployment of the prosthesis, or may be formed in the prosthesis as part of a deployment procedure. The various functions of the openings will be evident from the description below. In preferred embodiments of the invention, the sealing material is a foam cover that has a single hole.

The sealing material may be attached to the stent by any of a variety of connectors, including a plurality of conventional sutures of polyvinylidene fluoride, polypropylene, Dacron®, or any other suitable material and attached thereto. Other methods of attaching the sealing material to the stent include adhesives, ultrasonic welding, mechanical interference fit and staples.

One or more markers may be optionally disposed in or on the stent between the proximal end and the distal end. Preferably, two or more markers are sized and/or positioned to identify a location on the prosthesis, or to identify the position of the prosthesis, or a portion thereof, in relation to an anatomical feature or another system component.

First prosthesis is typically deployed in an arterial passageway upstream of an aneurysm, and functions to open and/or expand the artery, to properly position and anchor the various components of the system, and, in combination with other components, seal the system or portions thereof from fluid leaks. For example, the sealing prosthesis may be deployed within the infrarenal neck, between an abdominal aortic aneurysm and the renal arteries of a patient, to assist in repairing an abdominal aortic aneurysm.

Figure 2:
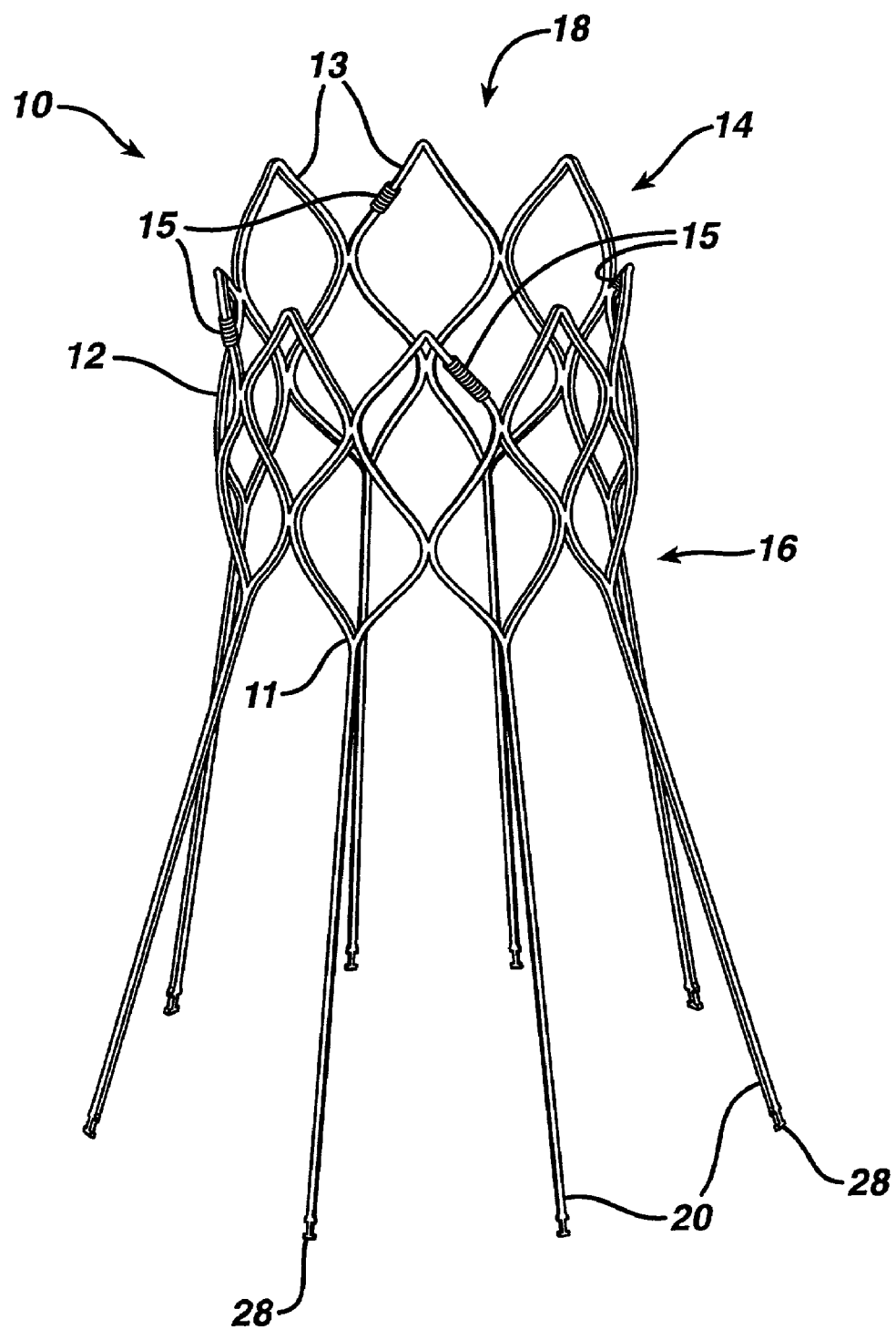
FIG. 2 is a perspective view of a stent for a first prosthesis, shown for clarity in an expanded state.
Figure 3:
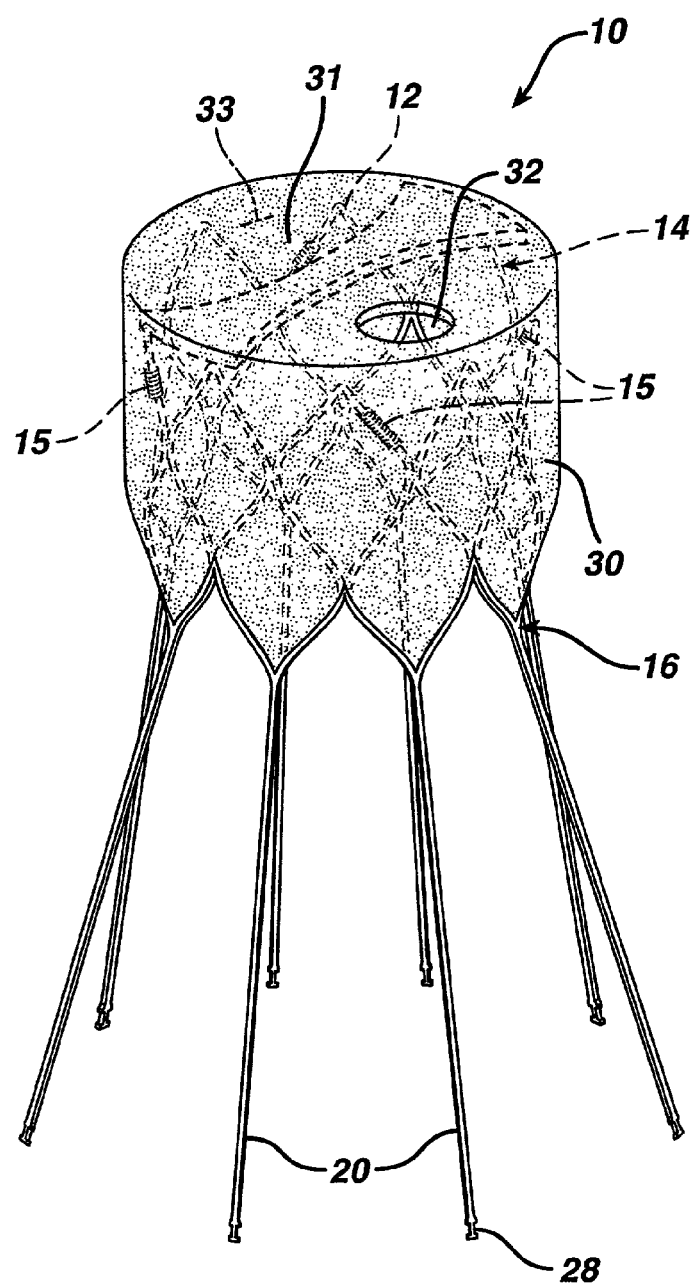
FIG. 3 is a perspective view of a first prosthesis having a stent covered by a gasket material.

FIGS. 1-3 show a first exemplary sealing prosthesis 10 in accordance with the present invention. Sealing prosthesis 10 includes a cylindrical or oval self-expanding lattice, support, or stent 12, typically made from a plurality of interconnected struts 13. Stent 12 defines an interior space or lumen 18 having two open ends, a proximal end 14 and a distal end 16. One or more markers 15 may be optionally disposed in or on the stent between the proximal end 14 and the distal end 16.

Stent 12 may further include at least two, but preferably eight (as shown in FIG. 2), spaced apart longitudinal legs 20. Preferably, there is a leg extending from each apex 11 of diamonds formed by struts 13. At least one leg, but preferably each leg, includes a flange 28 adjacent its distal end that, as is described in greater detail below, allows for the stent being retrievable into its delivery apparatus after partial or nearly full deployment of member 12 so that it can be turned, or otherwise repositioned for proper alignment.

FIG. 3 shows the sealing material 30 covering the proximal end of precursor stent 10. In the embodiment shown in FIG. 3, sealing prosthesis 10 includes a sealing material 30 having a first opening or hole 32 and a second opening or slit 33. The gasket material covers at least a portion of the interior or exterior of the stent, and most preferably covers substantially the entire exterior of the stent. For example, gasket material 30 may be configured to cover stent 12 from the proximal end 14 to the distal end 16, but preferably not covering longitudinal legs 20.

The sealing material helps impede any blood trying to flow around bypass prostheses 11a and 11b after they have been deployed (as shown in FIG. 1), and from flowing around the stent gasket 10 itself. For this embodiment, sealing material 30 is a compressible member or gasket located along both the interior and the exterior of stent 12.

FIGS. 10 and 11 show alternate configurations of first prosthesis 10 intended for use with arterial sections unsuitable for anchoring and/or sealing. The stent configurations shown in FIGS. 10 and 11 include a first portion, matrix or stent 12 configured to engage a portion of an artery 302 below the renal arteries (upstream of an aneurysm, see FIGS. 1 or 13), and a second portion, matrix or stent 106 configured to engage a portion of artery 302 above the renal arteries.

Figure 9:
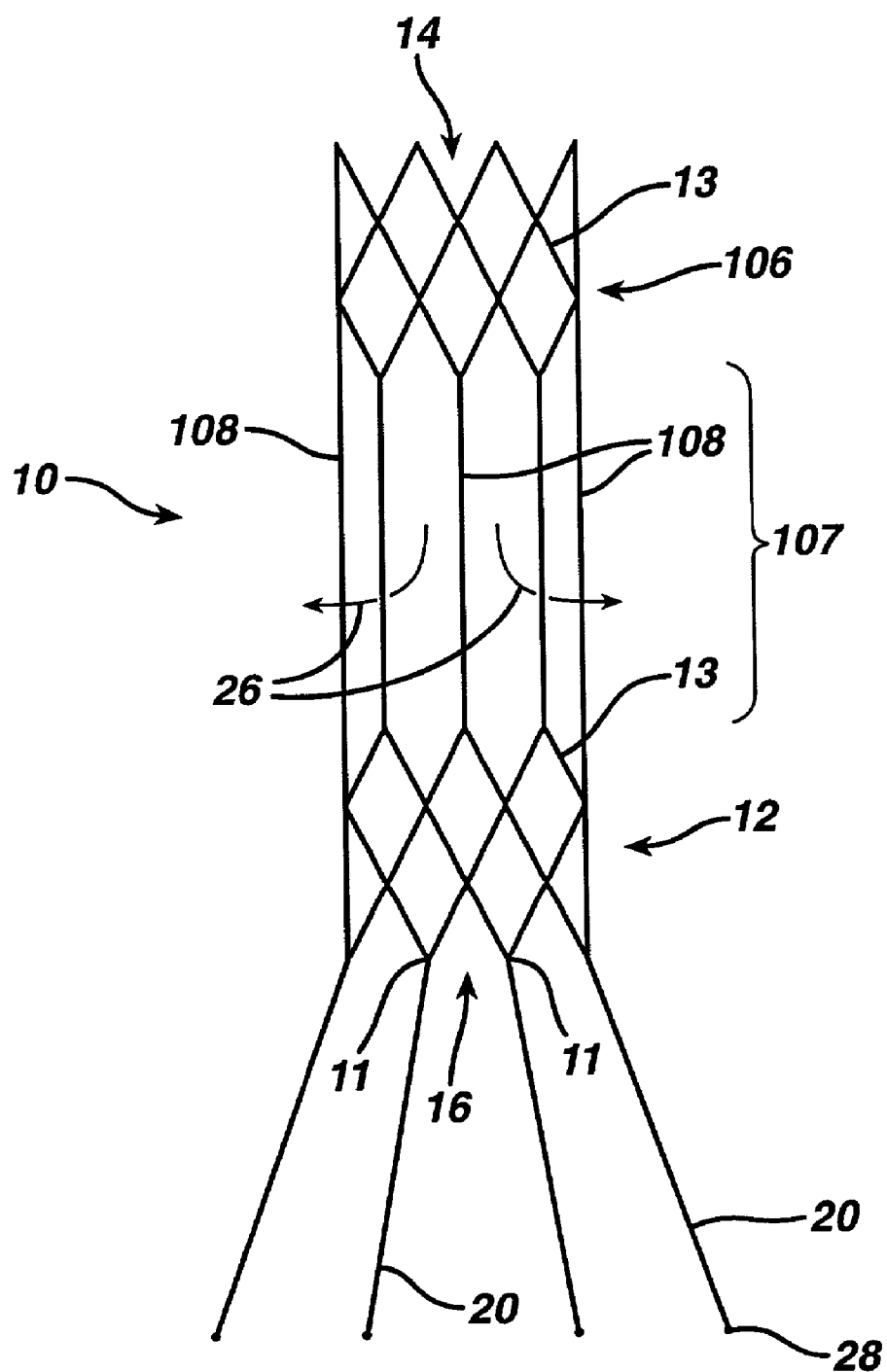
FIG. 9 is a side elevation of an embodiment of a stent of the present invention having an upstream extension anchor.

In these exemplary embodiments of the invention, the struts 13 or diamonds formed thereby, of matrix 12 include a proximally extending bridge 107 comprising at least one elongated strut 108 that communicates with or connects to the matrix 106. The exemplary embodiment of the invention shown in FIG. 9 includes a plurality of struts 108, preferably five, that in combination form a straight bridge. The exemplary embodiment of the invention shown in FIG. 10 includes a plurality of struts 108, preferably ten, that in combination form a jointed bridge, described in more detail below.

In some embodiments of the present invention, the first prosthesis 10, further includes a gasket member 30. This feature can be better understood by referring to FIGS. 1 and 3. Gasket member 30 covers one or more surfaces of stent 12, i.e., can be located along the interior or exterior of stent 12, or both. The gasket member helps impede any blood trying to flow around bypass prostheses 11a and 11b after they have been deployed (as shown in FIG. 1), and from flowing around the stent gasket 10 itself. For this embodiment, gasket member 30 is a compressible member located along both the interior and the exterior of stent 12. Gasket member 30 may be made from any number of materials known to those of ordinary skill in the art, including but not limited to open cell foam materials and closed cell foam materials. Exemplary materials include polyurethane, polyethylene, polytetrafluroethylene; and other various polymer materials, preferably woven or knitted, that provide a flexible structure. Highly compressible foams are particularly preferred, preferably to keep the crimped profile low for better delivery. Gasket 30 may be attached to stent 12 by any number of connectors, including a plurality of conventional sutures of polyvinylidene fluoride, polypropylene, Dacron®, or any other suitable material and attached thereto. Other methods of attaching gasket 30 to expandable member include adhesives, ultrasonic welding, mechanical interference fit and staples.

The first prosthesis may further include one or more occlusive members attached to the stent 12, and covering or extending across a predetermined portion of the interior of the stent. The occlusive member preferably covers only a portion of the interior of the stent in order to provide a guide or passageway from its downstream end to its upstream end, thereby maintaining an open channel or access to hole 32 and blocking the channel or access to opening 33 until needed. Preferably, the occlusive member blocks a portion of the lumen. The occlusive member may further include an opening or channel extending therethrough so as to receive a second guidewire for guiding a bypass prosthesis 11a to its proper position within the stent gasket.

In another exemplary embodiment, the occlusive member may stretch or cover the top of the stent and along its sides. In this embodiment of the invention, occlusive member may have a small opening or slit to accommodate the initial guidewire, and a larger opening for accommodating the second guidewire.

These occlusive structures promote proper side-by-side placement of one or more, preferably multiple, prostheses within the first prosthesis.

In the exemplary embodiments of the invention that include a stent configured as those shown in FIGS. 10 and 11, sealing material 30 preferably engages only the first portion 12 of stent 10. Alternately, sealing material 30 may also engage second portion 106 of stent 10. In the most preferred embodiments of the invention, bridge 107 may be open or may allow fluid cross flow, as is depicted by the arrows 26 in FIGS. 10 and 11. In these embodiments of the invention, sealing material 30 does not engage bridge 107, or the amount of graft material that engages bridge 107 does not prevent fluid cross flow. In other embodiments of the invention (not shown), sealing material 30 engages or covers bridge 107, but in this embodiment of the invention, the section of sealing material 30 that engages bridge 107 is porous, even more preferably, highly porous. It is intended that these various configurations of the stent and graft material should not impede or substantially impede the flow of blood through the first prosthesis and into arteries 3 or 4.

As noted above, the bridge section 107 interposed between the first matrix 12 and the second matrix 106 may be configured to accommodate a bend or highly angulated portion of an artery or other conduit. In accordance with the present invention, bridge section 107 may be variously configured to allow a prosthesis to have an angled configuration. One skilled in the art will readily recognize that the need for a prosthesis having an angled conformation may be dependent on a number of factors, including but not limited to, the specific pathological condition of the patient, the flexibility of a given prosthesis, stent, or assembly, and the purpose for which the prosthesis is being used, among others.

One skilled in the art will also recognize that some of the "straight" embodiments described above may be used in pathological conditions that involve or need an angled blood or fluid flow path. For example, a straight prosthesis may be used when only a small angle is involved. Any of the straight embodiments described above may be deformed to achieve an angled fluid flow path if the amount of deformation does not adversely affect the function of the prosthesis or the well being of the patient.

Conversely, one skilled in the art will recognize that a pathological or biological condition having a fluid flow path from a slight deflection to a wide angle (e.g., from about forty-five degrees to about ninety degrees or more) may warrant the use of a prosthesis having a structural configuration or element that allows the prosthesis to achieve the angled configuration. In these situations, it is believed that the following are exemplary embodiments of the invention that would provide beneficial results in achieving a fluid flow path through a tortuous channel.

A prosthesis having an angled conformation may be achieved by interposing one or more pivots, joints, axes, junctions, hinges, narrows, hubs, or the like, in the struts 108 or the bridge 107 between matrix 12 and matrix 106. Individual struts 108 may be joined or connected at this joint, as is shown in FIGS. 11a, 11b and 11c, various configurations that allow a prosthesis or stent to achieve an angled conformation.

In preferred embodiments of the invention, an intermediate section of the bridge 107 includes a pivot 120 or hinge. Pivot 120 in FIG. 11c, and similar configurations, allow some degree of movement between the struts of the bridge, i.e., the angle between adjacent struts is moveable or changeable.

Figure 11A:
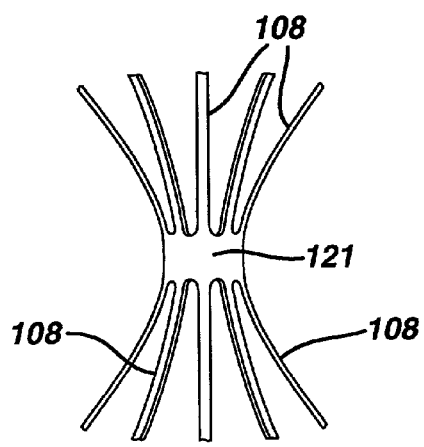
FIGS. 11(a-c) show alternative embodiments of an angle junction for the stent of FIG. 10.
Figure 11B:
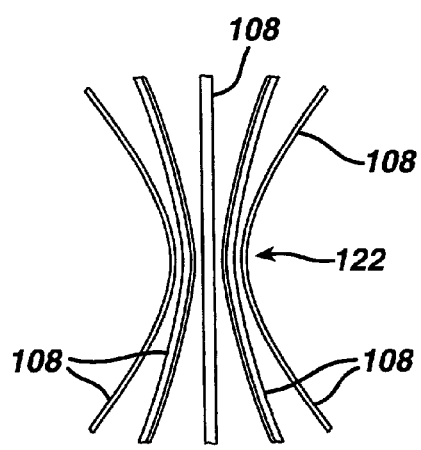
Figure 11C:
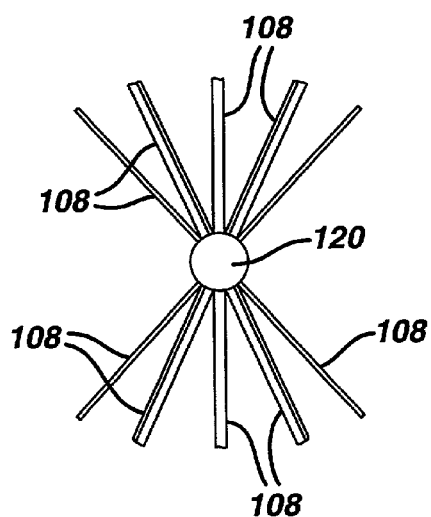
Figure 12A:
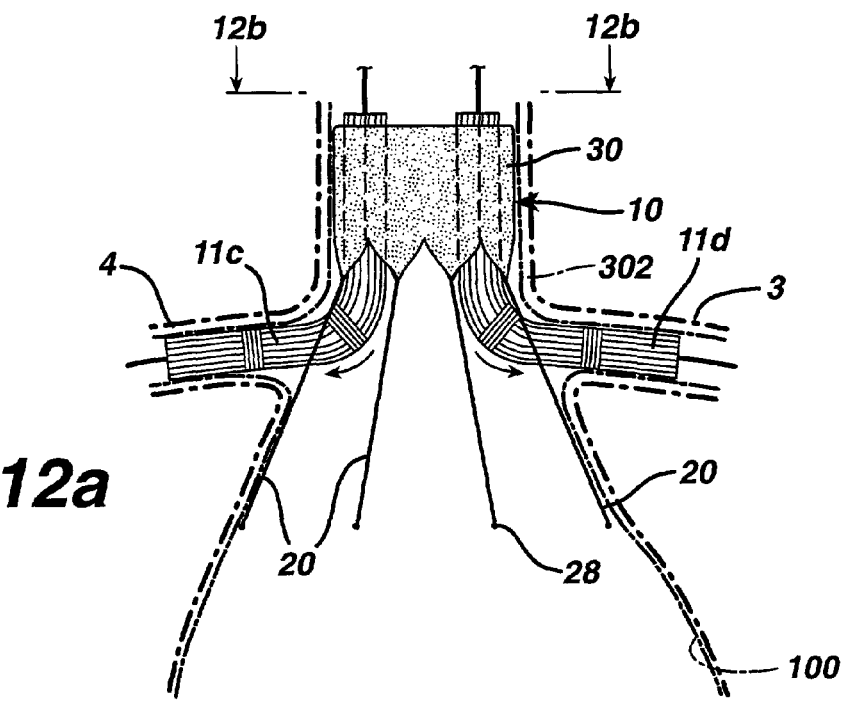
FIGS. 12a-12d show a method of delivering and deploying an alternative system according to the invention having a first prosthesis and four bypass prostheses.
Figure 12B:
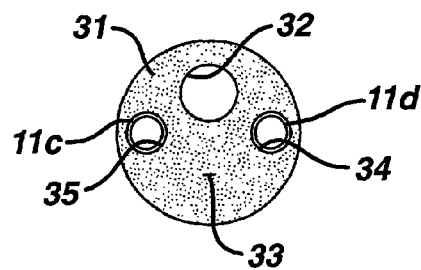
Figure 12C:
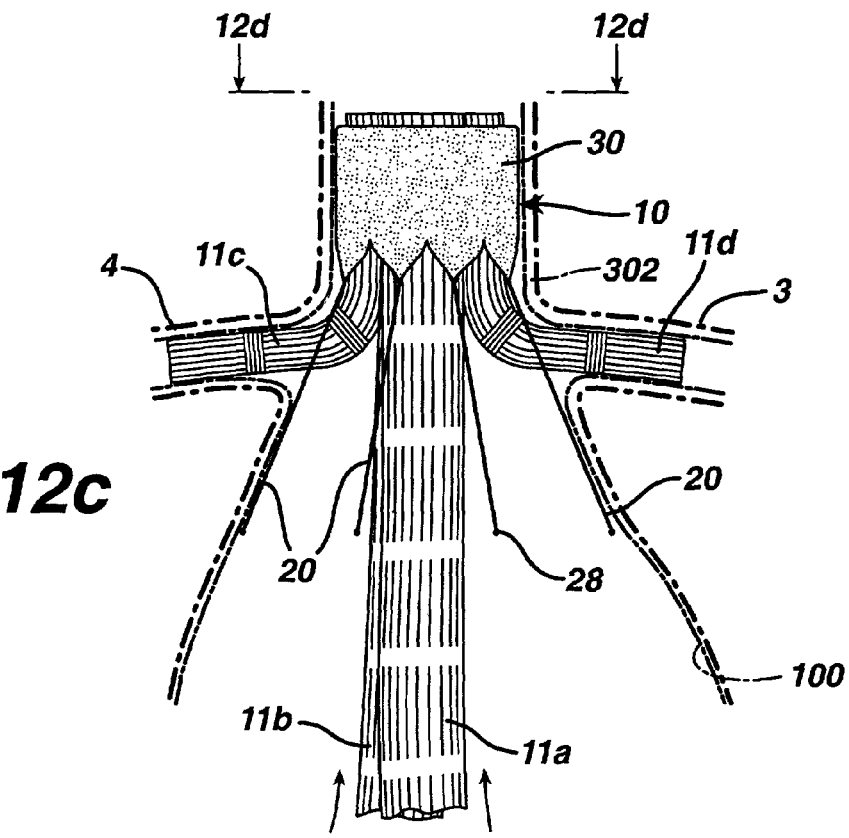
Figure 12D:
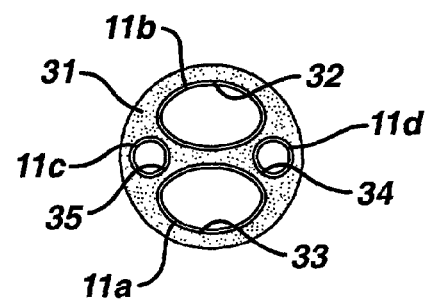

The present invention also includes a prosthesis or stent having an intermediate section of the bridge 107 that comprises a joint, junction, or hub 121 in which the struts are fixed together at the intermediate section, as illustrated in FIG. 11a.

The present invention also includes a prosthesis or stent having an intermediate section of the bridge 107 that comprises a narrow or corseted configuration 122 in which a portion of the struts 108 are positioned in close proximity to a portion of another strut. The exemplary embodiment in FIG. 11b shows an intermediate portion of the struts in close proximity to each other.

An alternate embodiment of the present invention uses a first prosthesis 10 as described for FIGS. 1 and 3, and positions it across an arterial junction, as shown in FIG. 13. As is readily evident to one skilled in the art, a system that includes a first prosthesis 10 upstream of both an aneurysm and cross arteries will preferably include a number of additional prostheses for establishing alternative fluid flow paths. In these embodiments of the invention, first prosthesis 10 preferably includes sealing material 30, cover 31 (FIGS. 12a-d), and/or an occlusive member configured to receive one or more additional system components. In the exemplary embodiment shown in FIG. 13, the system includes two second prostheses, 11a and 11b, and two additional second or bypass prostheses 11c and 11d.

As shown in FIGS. 12a-d, sealing material 30 and/or cover 31 may be configured to receive one or more additional system components by including one or more slits, holes, passages, cavities, or the like. Preferably, any structure configured to receive another system component will be deformable or resilient to sealingly engage a portion of the system component as is discussed in detail subsequently.

Second Prosthesis

The second prosthesis is a bypass conduit or the like that is typically deployed in an arterial passageway upstream of an aneurysm, and extends from a healthy portion of the artery, through the arterial segment having the aneurysm, and into another healthy portion of the artery or another artery. The second prosthesis functions to bypass the portion of the conduit containing the aneurysm, and to properly position and/or anchor the upstream end of the system in an artery. The second prosthesis may also include one or more structures for positioning and anchoring the second prosthesis in the artery or in the first prosthesis. In a preferred embodiment of the invention, the second prosthesis is adapted to engage the first prosthesis.

The second prosthesis typically includes a support matrix or stent that supports a graft material. One end of the second prosthesis is typically adapted to engage one or more portions of first prosthesis. In preferred embodiments of the invention, the upstream end of second prosthesis is adapted to matingly engage an upstream portion of first prosthesis. The second prosthesis may optionally include at least one attachment structure on its downstream end for engaging and securing the prosthesis in a portion of an artery downstream of the aneurysm. In accordance with some embodiments of the invention, the second prosthesis may include an intermediate portion having a branch leg extending therefrom.

One or more markers may be optionally disposed in or on the prosthesis between the upstream end and the downstream end. Preferably, two or more markers are sized and/or positioned to identify a location on the prosthesis, or to identify the position of the prosthesis, or a portion thereof, in relation to an anatomical feature or another system component. In preferred embodiments of the invention, fluoroscopically identifiable sutures or staples are used; these sutures or staples may also attach the graft material to the stent.

Figure 4:
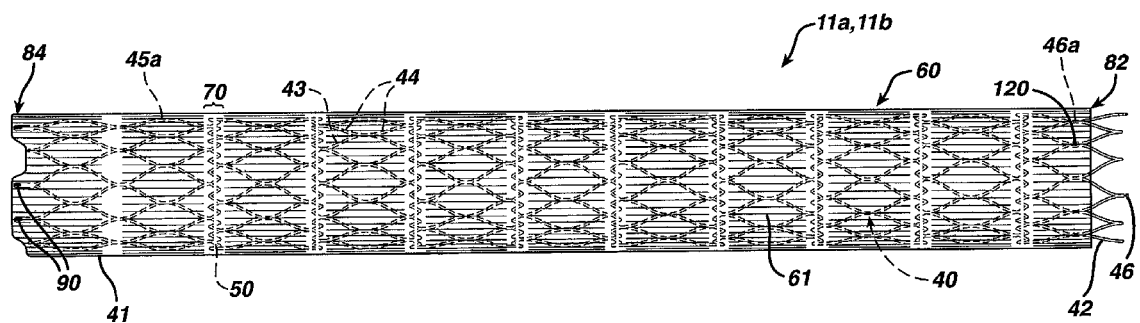
FIG. 4 is a side elevation of a second prosthesis having a stent covered by a graft material.

FIGS. 1, 4, 4a, 8, and 13 show exemplary second or bypass prostheses 11a,b of the present invention. As shown in FIGS. 1, 4 and 8, second prosthesis 11a,b includes a substantially cylindrical self-expanding lattice, support, or stent 40, typically made from a plurality of interconnected struts 44. Lattice 40 defines an interior space having two open ends, an upstream end 41 and a downstream end 42. The interior and/or exterior surfaces of lattice 40 may be covered by or support at least one graft material 60.

FIGS. 12a, 12b, 12c, 12d and 13 show exemplary additional second prostheses having 11c and 11d in accordance with the present invention. In FIGS. 12a-d and 13, the additional second prosthesis 11c, 11d is shown engaged with first prosthesis or stent gasket 10. The foregoing and other features of the second prosthesis will be described in more detail below.

Third Prosthesis

A third prosthesis may have the construction of either of the second prostheses described above, depending upon the environment in which the system repair device is to be used. For example, as illustrated in FIG. 8, the third prosthesis 11e is a bypass conduit or the like matingly engaged with the second prosthesis 11b and deployed in an arterial passageway extending through an aneurysm in the common iliac artery, to a healthy portion of an internal iliac artery. The third prosthesis further includes a branch leg 11g (see also FIG. 4a) that functions to establish a fluid flow path or channel off of the third prosthesis 11e, f and into an exterior iliac artery downstream of the aneurysm in the common iliac. An extension prosthesis or cuff may be attached to branch leg 11g to provide deeper access into the exterior iliac artery, if desired. The third prosthesis may also include one or more structures for positioning and anchoring the third prosthesis in the artery or to the second prosthesis. In a preferred embodiment of the invention, the third prosthesis is adapted to matingly engage the second prosthesis.

In keeping with a feature of the invention, third prosthesis 11e, f may comprise an extension cuff, engaged with the downstream end of second prosthesis 11b. Third prosthesis 11e, f defines a fluid flow path into one of the external iliac arteries 123 or 126. The corresponding internal iliac 124 or 125 may be provided with an embolic device such as a coil to occlude flow. However, in a particularly preferred embodiment, third prosthesis 11e, f includes a branch leg 11g that may be positioned in the internal iliac creating a fluid flow path into the internal iliac.

Any third prosthesis may be configured as described above for any second prosthesis.

Stent

Any of the stents of the present invention form a support or lattice structure suitable for supporting a graft material. In preferred embodiments of the invention, the stent defines a channel through which a fluid, such as blood, may flow. A typical stent comprises an expandable lattice or network of interconnected struts. In preferred embodiments of the invention, the lattice is fabricated, e.g., laser cut, from an integral tube of material.

In accordance with the present invention, the stent may be variously configured. For example, the stent may be configured with struts or the like that form repeating geometric shapes. One skilled in the art will readily recognize that a stent may be configured or adapted to include certain features and/or to perform a certain function(s), and that alternate designs may be used to promote that feature or function.

In some exemplary embodiments of the invention, the struts of the stent gasket form a matrix having diamond shapes. In the embodiment of the invention shown in FIG. 2, the matrix or struts of stent 10 are configured into a diamond shapes, preferably having approximately eight diamonds. In a most preferred embodiment of the invention, the fully expanded diamond pattern of a first prosthesis has angles of about forty-five to fifty-five degrees at their downstream and upstream ends.

In the exemplary embodiment of the invention shown in FIG. 4, the matrix or struts of stent 40 may be configured into at least two hoops 43, each hoop 43 comprising a number of struts 44 having a diamond shape, and having approximately nine diamonds. A second and/or third prosthesis, such as second and third prostheses 11a, b, c, d, e, f, may further include a zigzag shaped ring 50 for connecting adjacent hoops to one another. The zigzag shaped rings may be formed from a number of alternating struts 52, wherein each ring has fifty-four struts.

The diamond pattern provides the hoops with radial and longitudinal stiffness. The longitudinal strength provides for better mechanical fixation of stent 40 to a graft material (described below). The radial strength provides the upstream hoop 45a with better attachment and sealing to stent gasket 10, and provides the downstream hoop 45b with better fixation and sealing to the arterial wall. Further, the downstream hoop may be flared, and may be exposed after the graft material has been attached to the stent.

In one preferred embodiment, the upstream and downstream hoops have greater radial and longitudinal strength than the hoops therebetween. This creates a stent graft having stiff ends for anchoring, but a more flexible body for navigation through the vasculature. The stiffer ends may be accomplished by changing the dimensions of the struts for the end hoops, or by varying the heat treatment of the end hoops during manufacture. The rings allow the stent to bend more easily, and generally provide for more flexibility when the stent is being delivered through a tortuous vessel. When a non-compliant graft is attached to stent 40, the strength of the diamond hoops scaffolds any graft folding into the blood flow lumen, while maintaining a tight kink radius.

Some embodiments of a prosthesis according to the present invention may include one or more anchors and/or one or more struts of the stent configured into an anchor. Typically, one or more anchors are used to engage, position, or attach a prosthesis in the artery. One or more anchors, commonly referred to as recapture legs, may also be configured to releasably engage a delivery device, such as a catheter, or a portion thereof.

The downstream end of the stent is preferably configured to engage a complementary structure on a delivery device, such as a catheter or a portion thereof. For example, the downstream end of the stent may include one or more keys that engage, preferably releasably engage, a corresponding latch on the catheter. An exemplary configuration is shown in FIG. 7. It is intended that the invention should not be limited by the precise structures used to engage the stent to the delivery device.

In the embodiments of the invention shown in the Figures, the stent may include one or more anchors 28 (FIGS. 1, 2 and 3), 46 (FIGS. 4, 4a, 4b and 7) configured to engage a corresponding structure on a delivery device 130 (illustrated most clearly in FIG. 7). In accordance with the present invention, the delivery apparatus may include a collar having one or more grooves or the like adapted to releasably engage one or more complementary structures on a stent or prosthesis of the present invention. For example, the delivery apparatus 130 shown in FIG. 7 includes three grooves 144 to configure the delivery device to releasably engage the second prosthesis 11a, 11b (having three anchors 46), and the third prosthesis 11e, 11f and branch leg 11g and extension cuff 11h (having three anchors 46). A similar device having eight grooves may be utilized to releasably engage the first prosthesis 10 (FIG. 1) which has eight anchors 28 (FIG. 5). Such an anchor/delivery device configuration is particularly suited to partially deploying a prosthesis of the present invention, and to position or re-position the prosthesis.

Any of the stents of the present invention may be formed of any material suitable for functioning in vivo as a support for graft material. A stent of the present invention may be formed of a wide variety of materials, all of which are well known to those skilled in the art. In some embodiments of the invention, the stent is formed from a metal or metal alloy. In preferred embodiments of the invention, the stent is formed from superelastic Nickel Titanium alloys (Nitinol). Descriptions of medical devices that use such alloys can be found in U.S. Pat. No. 4,665,906 and European Patent Application EP 0928606, both of which are hereby incorporated herein by reference. A stent according to the invention is preferably laser cut from a tubular piece of Nitinol and thereafter treated so as to exhibit shape memory and superelastic properties at body temperature. In preferred embodiments of the invention, the stent material is expandable or collapsible, i.e., moveable from a first closed position to a second open position, or vice versa.

In accordance with some embodiments of the present invention, the upstream and/or downstream end of a stent may include one or more anchors and/or one or more struts of the stent configured into an anchor. One or more anchors may also be configured to releasably engage a delivery device, such as a catheter, or a portion thereof.

Figure 4A:
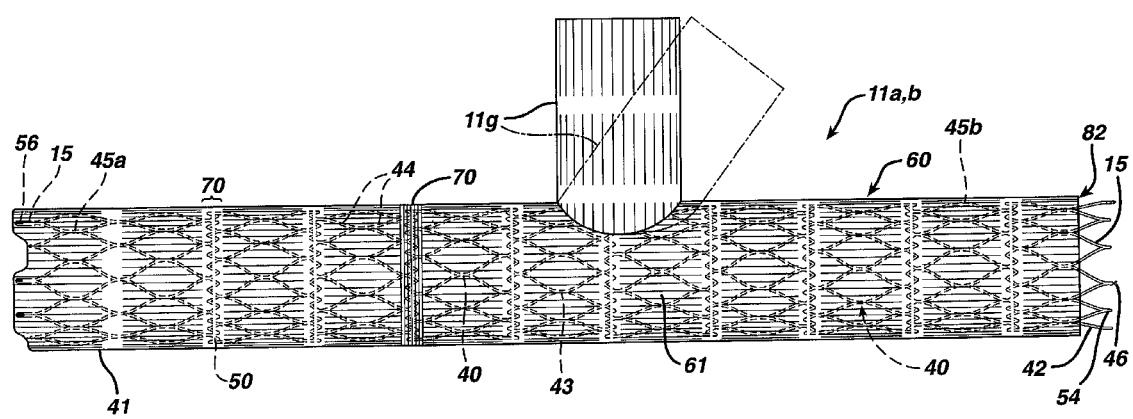
FIG. 4a is a side elevation of a prosthesis having a branch leg.
Figure 4B:
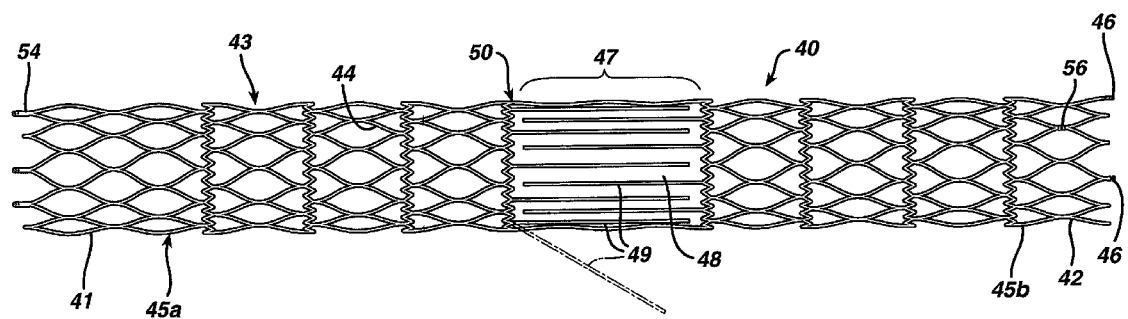
FIG. 4b is a side view of the matrix of FIG. 4a without the graft materials illustrating radially disposed antennae.

In keeping with a particularly preferred aspect of the invention, the stents that comprise the extension prostheses, e.g., the second, third, fourth, prostheses, may be configured as described below. FIGS. 4a and 4b best show stents equipped with branch legs in accordance with the invention. The stents illustrated in FIGS. 4a and 4b are similar to the stents described above. However, the matrix of stent 40 includes an intermediate portion 47 including an aperture 48. Branch leg 49 extends from the perimeter of aperture 48 to form the skeletal structure of an alternate conduit. Branch leg 49 preferably comprises a plurality of relatively long, wide, straight struts. The struts are preferably long enough to be seated in or next to a bifurcated or cross artery in a manner sufficient to permit direct fluid flow to the bifurcated or cross artery. An extension prosthesis may matingly engage the branch leg to facilitate this fluid flow path. However, the strut length may be varied in accordance with the desired application. The struts are preferably wide enough to form a skeletal structure supporting a graft material (to be described in more detail below). However, the strut width may be varied in accordance with the desired application. The number of struts also may be chosen according to the intended use of stent 40.

In keeping with a preferred feature of the invention, branch legs 49 may be shape set such that each strut forms an angle with the longitudinal axis of stent 40. Preferably, branch legs 49 are shape set as appropriate to the condition being treated. Shape setting may be performed according to generally known techniques for working shape memory materials. Each strut is preferably shape set to form a substantially identical angle with respect to the longitudinal plane. Alternately, each strut may have a unique orientation. In a particularly preferred embodiment of the invention, branch legs 49 are shape set substantially perpendicular to the longitudinal axis to accommodate cross-vessels positioned substantially perpendicular to the vessel being treated.

Aperture 48 may be disposed along stent 40 as appropriate for the condition being treated. Aperture 48 may be centered, as illustrated in FIG. 4b, or off-center. In addition, stent 40 may be provided with additional apertures 48 and associated branches 49. In such a manner, a single stent 40 may include multiple branch legs.

Graft Material

An inner or outer surface of a stent of the present invention may be covered by or support a graft material. Graft material 60 (FIGS. 4, 4a, 6 and 7) can be made from any number of materials known to those skilled in the art, including woven polyester, Dacron®, Teflon®, polyurethane, porous polyurethane, silicone, polyethylene terephthlate, expanded polytetrafluoroethylene (ePTFE) and blends of various materials.

In some embodiments of the invention, it may be desirable to incorporate a biodegradable, or degradable material, such as albumin, collagen, or any type of collagen. A graft material that is biodegradable would erode or dissolve over time; it is believed that the eroding graft material may be replaced by one or more biofusion constituents.

The graft material may be variously configured, preferably to achieve predetermined mechanical properties. For example, the graft material may incorporate a single or multiple weaving and/or pleating patterns, or may be pleated or unpleated. For example, the graft may be configured into a plain weave or a satin weave, may include continuous longitudinal pleats, interrupted pleats, annular or helical pleats, radially oriented pleats, or combinations thereof.

Alternately, the graft material may be knitted or braided. In the embodiments of the invention in which the graft material is pleated, the pleats may be continuous or discontinuous. Also, the pleats may be oriented longitudinally, circumferentially, or combinations thereof.

As shown in FIG. 4, graft material 60 may include a plurality of longitudinal pleats 61 extending along its surface, generally parallel to the longitudinal axis of the prosthesis. As shown in FIG. 6, the pleats allow the prosthesis to collapse around its center, much as it would be when it is delivered into a patient. As illustrated, the pleats come together as a series of radially oriented regular folds 68 that pack together efficiently. This provides a relatively low profile delivery system, and provides for a controlled and consistent deployment therefrom. It is believed that this configuration minimizes wrinkling and other geometric irregularities. Upon subsequent expansion, the prosthesis assumes its natural cylindrical shape, and the pleats or folds uniformly and symmetrically open.

In addition, pleats 61 help facilitate stent graft manufacture, in that they indicate the direction parallel to the longitudinal axis, allowing stent to graft attachment along these lines, and thereby inhibiting accidental twisting of the graft relative to the stent after attachment. The force required to push the stent-graft out of the delivery system may also be reduced, in that only the pleated edges of the graft make frictional contact with the inner surface of the delivery system. One further advantage of the pleats is that blood tends to coagulate generally uniformly in the troughs of the pleats, discouraging asymmetric or large clot formation on the graft surface, thereby reducing embolus risk.

As shown in FIGS. 4 and 4A, the graft material may also include one or more, and preferably a plurality of, radially oriented pleat interruptions 70. The pleat interruptions are typically substantially circular and are oriented perpendicular to longitudinal axis. Pleat interruptions 70 allow the graft and prosthesis to bend better at selective points. This design provides for a graft material that has good crimpability and improved kink resistance.

As noted above, the extension prosthesis may be pleated longitudinally, axially, or combinations of both. Under typical conditions, these pleats will form a relatively consistent pattern, e.g., pleats all of a certain length. In the embodiments of the present invention for use in a highly angulated artery, it may be desirable to vary the pattern or patterns of pleats. For example, in the area of greatest angle, it may be desirable to provide an extension prosthesis having one or two (or more, as needed) pleat interruptions or axially pleated sections separated by a shorter longitudinally pleated section or sections. It is believed that increasing the number of axial pleats in the highly angulated section of the artery reduces stress on the prosthesis, and may promote a more fluid tight fit of the system.

The graft material as described above is preferably highly compressible, which also promotes a low crimped profile for better delivery characteristics.

In accordance with the present invention, the graft material may be impervious or substantially impervious to the flow of blood, or may be porous. A graft material is impervious if it prevents blood from passing through the graft material on contact with blood or after the graft material is saturated with blood. Choice of the flow characteristics of a graft material are well known to those skilled in the art, and are tied in part to the intended function of the prosthesis or portion of the prosthesis. For example, it may be desirable for the graft material that forms the cover of the first prosthesis to be impervious or substantially impervious to the flow of blood. Alternately, it may be desirable for a graft material to be porous or partially porous to promote biofusion.

In addition, it is preferable that the gasket member be substantially impervious to the flow of blood, at least when in a partially compressed state. When used throughout for the present invention, materials that are substantially impervious to the flow of blood include materials that become substantially impervious to the flow of blood after being saturated with blood.

The foregoing graft materials can be knitted or woven, and can be warp or weft knitted. If the material is warp knitted, it may be provided with a velour, or towel like surface, which is believed to speed the formation of blood clots, thereby promoting the integration of a prosthesis or prosthesis component into the surrounding cellular structure.

A graft material may be attached to a stent or to another graft material by any number of structures or methods known to those skilled in the art, including adhesives, such as polyurethane glue; a plurality of conventional sutures of polypropylene, Dacron®, or any other suitable material; ultrasonic welding; mechanical interference fit; and staples.

As stated above, a stent preferably has a graft member attached thereto. The graft member covers at least a portion of the interior or exterior of the stent, and most preferably covers substantially the entire exterior of the stent. In some embodiments of the invention, prosthesis 11a, b, c, d, e, f, g, h includes graft material 60 that covers only a portion of the downstream end 42 of matrix 40. See, for example, FIG. 4.

In an alternate design, graft material may not be utilized on either end of the stent. For example, on any endolegs, prostheses, extension cuffs, stent gaskets or other covered stents, both ends thereof may be left uncovered. The body has the ability to cover the exposed portions of the stent with endothelial cells and thus these exposed portions become endothelialized or incorporated into the vessel wall. This may be an important factor in the long-term stability of the system. Essentially, over long periods of time, the aneurysmal sac can and will shrink if it is totally excluded from blood flow. This shrinkage changes the morphology of the aortic region that has been treated with the bypass prostheses. If all ends of the system are firmly anchored in the actual vessel, as is the case when the ends are covered with endothelium cells, the system will be better able to withstand these morphological changes.

Stent 40 illustrated in FIG. 4b is also provided with a graft member, best shown in FIG. 8. The graft member may be of a conventional bifurcated design having a tubular member structure surrounding the main leg of stent 40 and an offshoot attached to and surrounding branch 49. The graft member and branch 49 together form a branch leg, e.g., branch leg 11g.

In accordance with the present invention, it may be highly desirable to provide a graft material that limits or eliminates the amount of blood that passes between the graft and the arterial wall, to provide a catheter-delivered graft or prosthesis that extends through a longer portion of an artery, to improving the anchoring mechanisms between two prostheses, to improving the anchoring mechanism between the prosthesis and the arterial wall or an interluminal cavity within an artery, and to improve the fluid dynamic and performance characteristics if the implanted prosthesis.

Marker

As noted above, a stent and/or prosthesis of the present invention may include one or more markers. One skilled in the art will recognize that one or more markers may be positioned on the stent, the graft material, or on the prosthesis. In preferred embodiments of the invention, the markers are used to identify the position of the stent or prosthesis in relation to a body part and/or in relation to another stent or prosthesis, and/or to identify the position of one part of the prosthesis relative to another part. In most preferred embodiments of the invention, the marker(s) is used to identify a position in vivo.

As shown in FIGS. 2-4a, a stent, such as stents 12 and/or 40, preferably includes one or more radiopaque markers 15. Exemplary materials for forming markers include but are not limited to tantalum, platinum, iridium, and gold. As shown, markers 15 are coils of radiopaque metal, wrapped around the struts of the stent. Markers 15 are preferably made from 0.0075" diameter tantalum (Ta) wire wrapped tightly around the struts. The number, location, and size of the markers may vary, and the markers may be used alone or in combination to identify the position of a particular portion of the prosthesis. For example, with respect to FIG. 3, a downstream marker adjacent aperture 32 may be 5 mm long and the downstream marker adjacent hole 33 may be 2 mm long. Also, two downstream markers may be one hundred eighty degrees apart, and an upstream marker may be positioned equidistant from each of the downstream markers. In this exemplary configuration, the upstream marker then aids proper rotational positioning of the device.

Connectors

Some embodiments of a prosthesis according to the present invention may include one or more connectors. In some embodiments of the invention, the connectors are used to engage or connect one prosthesis or component to another. In some embodiments of the invention, the connectors may be used to attach the graft material to a stent or lattice.

As noted above, one skilled in the art will recognize that a variety of materials and methodologies may be used to connect one prosthesis to another, or to attach the graft material to a stent. Exemplary connectors include but are not limited to sutures, staples, rivets, or the like. In preferred embodiments of the invention, the connector is a suture or staple, even more preferably, having a knotted or nub end. Further, a connector may be formed from a radiopaque material or a fluorescent material, each of which allow the connector to be used as a marker.

In accordance with the present invention, it may be desirable to incorporate in a prosthesis a connector adapted for use with a lattice-like stent. A first connector 54, an exemplary embodiment of which is shown in FIG. 4a, is configured for use at an end portion of a stent, preferably at an end portion of a strut 44. A second connector 56, an exemplary embodiment of which is shown in FIGS. 4a and 7, is configured for use at an internal portion of a stent, preferably at the junction between two struts 44.

A connector configured for receiving a rivet, staple, suture, or the like, may include two apertures, each aperture configured to receive a leg of the rivet, staple, suture, or the like. In this embodiment of the invention, the end of each leg is preferably formed into a knot, nub or spherical end that is of larger diameter than the diameter of the aperture. Preferably, all of the elements noted above are assembled, the legs are passed through the apertures, and the end of each leg is formed into a nub. Alternately, one end may be formed into a nub prior to placement through the aperture, with the second end being formed into a nub after assembly of all the elements.

The number of connectors and staples are typically dictated by the size and structure of a particular stent; it is intended that the invention should not be limited thereby. The illustrated embodiments show six first connectors and three second connectors.

The above staple aperture design or connector assembly has many advantages for attaching gasket material or a graft material to a stent. Because the legs of the staple are folded around and imbedded within a pocket or the like, any risk of puncturing an inflation balloon is minimized. In addition, the structural integrity of the prosthesis is increased because staples more securely attach the graft material to the stent, as compared to prior art designs that use suture or adhesives to attach the graft to the stent.

Staples 90 and 120 (in FIGS. 4 and 7) may be made from any number of materials known in the art, including tantalum alloys, platinum alloys or stainless steel, such as a grade of type 316 stainless steel. The staples may take on other configurations and shapes, and can be coated for lubricity purposes. The staples may be formed from a radiopaque material to identify the location of the staple, and to act as a marker to identify the location of a portion of the prosthesis. Using a different number of radiopaque staples on a downstream end of a stent as compared to an upstream end further assists in identifying the position of the prosthesis.

Methods

A method in accordance with the present invention includes delivering and positioning a system or component of a system in a fluid conduit, such as an aorta and an iliac artery. The components described above permit intraluminal delivery into an aorta and an iliac artery. This is accomplished by percutaneously inserting the prostheses into the same or different arteries, e.g., a common femoral artery, and navigating them to the site of the aneurysm or aneurysms. This type of procedure is similar to delivery of angioplasty catheters and guiding catheters into the human vasculature. Upon proper positioning, the system components may be deployed either through a radially, outwardly extending force, e.g., expanding a balloon, or, if a self-expanding stent, by releasing the stent anchors from a constraint. Once fully deployed, at least one passageway is formed bypassing the aneurysm or aneurysms. As shown in FIG. 1, it may be desirable to form two fluid flow paths bypassing the aneurysm, each fluid flow path extending into a separate downstream artery.

In preferred embodiments of the invention, the first prosthesis is a stent gasket, even more preferably, a stent gasket that expands automatically against the wall of the artery. As the stent gasket expands, proximal longitudinal legs anchor the precursor stent in place. The method also includes delivering and positioning at least one second prosthesis. In preferred embodiments of the invention, the second prosthesis is a bypass conduit for extending through an aneurysm. The second prosthesis is typically positioned within the first prosthesis, preferably into and through a hole in the first prosthesis cover. In most preferred embodiments of the invention, the hole is slightly smaller in diameter than the expanded diameter of the second prosthesis, thus sealingly engaging the second prosthesis in the first prosthesis. The sealed configuration of the second prosthesis within the first prosthesis forms a fluid pathway through the assembly or system, thereby bypassing the aneurysm.

For embodiments of the invention as illustrated in FIG. 8, the method may further include delivering and positioning at least one third prosthesis 11e in the iliac artery 1. In preferred embodiments of the invention, the third prosthesis 11*e* is a bypass conduit for matingly engaging with the second prosthesis 11*b* and extending from the downstream end of the second prosthesis into the iliac artery 1. The third prosthesis 11*e* may further include a branch leg 11*g* so the third prosthesis 11*e* should be positioned within the iliac artery 1 such that the branch leg 11*g* is deployed in one of the external and internal iliac arteries 123, 124 and the main leg is deployed in the other of the external and internal iliac arteries 123, 124. The third prosthesis forms a first fluid pathway or channel through a common iliac artery into one of the internal and external iliac arteries, thus bypassing the aneurysm disposed in the common iliac artery. In addition, the branch leg of the third prosthesis creates a second fluid flow path from the common iliac artery into the other of the internal and external iliac arteries.

FIGS. 1, 5, 7, 8, 12*a*, 12*b*, 12*c*, 12*d* and 13 generally show how the system of the present invention may be deployed in vivo. A suitable delivery device, such as a catheter, may include a guidewire defining a path for prosthesis deployment and a collar or the like that releasably engages at least one anchor on the prosthesis. Once the anchors are released from the collar, the prosthesis can expand, preferably automatically. The portion of the delivery device containing the collar can then be removed from the artery, typically leaving the guidewire in place. The guidewire can then be used to guide another prosthesis or prostheses into position.

In some embodiments of the invention, the collar of the delivery device, engaged to the prosthesis, may be positioned within a sheath or the like until the prosthesis is delivered. In preferred embodiments of the invention, the sheath covers the prosthesis and helps crimp the prosthesis to a low profile, and a portion of the prosthesis may be partially deployed and/or positioned.

In accordance with a particularly preferred aspect of the invention, the sheath may cover the prosthesis illustrated in FIG. 4*b*. Due to its superelastic properties and structural continuity with stent 40, branch leg 11*g* is easily and closely crimped with stent 40 by the sheath. Once it is determined that the prosthesis is in its proper position, the collar can be pushed out of the sheath, thereby releasing the anchors from the collar. If the prosthesis is a self-expanding prosthesis, release of the flanges will allow the prosthesis to deploy automatically. If the prosthesis includes a branch leg, then the branch leg will automatically deploy along with the prosthesis. If the prosthesis is not self-expanding, a deflated balloon or the like may be delivered to the interior of the prosthesis using the guidewire. When the balloon is inflated, it will expand the prosthesis into its fully deployed position, i.e., fully expanded radially.

As is evident to one skilled in the art, precisely placing a component(s) of the system may be critical. The physician must have precise placement of the components to ensure adequate repair of the aneurysm. The present invention allows the physician to fully deploy a component within the body without fully releasing the entire component from the delivery device. The anchors releasably interlock with complementary structures, such as grooves, on the delivery device, and, if the physician decides that the placement of the component is incorrect, the outer member of the delivery device may be moved relative to an inner member, thereby resulting in the prosthesis being retrieved or retracted within the delivery device. The extended legs and anchors allow the physician to temporarily position the prosthesis before full deployment. Once the physician is satisfied with a prosthesis' position, the legs 20 may be released from their engagement with the delivery device.

In order to prevent the physician from prematurely completely deploying a prosthesis, a releasable stop may be preferably placed on the delivery device.

After proper delivery, stent gasket 10 and prostheses 11*a*, *b*, *c*, *d*, *e*, *f*, *g*, *h* should appear as they do in FIGS. 1, 8, and 13. Stent gasket 10 along with its attached graft material 30 and cover 31 are firmly secured within an arterial section upstream of an aneurysm, and may or may not extend into one or more arteries. For example, the first prosthesis or a portion thereof may be positioned upstream of an arterial junction (FIG. 13) or downstream of the junction (FIG. 1). Second prostheses 11*a* and 11*b* provide a first fluid flow path that extends through the aneurysm, anchoring in an artery downstream of the aneurysm and a second fluid flow path extending through and anchoring in a second artery either downstream or upstream from the aneurysm 100 (FIGS. 1 and 13). Third prostheses 11*e* and 11*f* provide separate fluid flow paths that extend through arteries disposed downstream from aneurysm 100, which arteries may themselves include aneurysms 207 and 208, respectively (FIG. 8).

A preferred embodiment of the invention is designed to treat Type IIC abdominal aortic aneurysms where aneurysms have developed in the common iliac arteries that extend to the iliac bifurcation. A proximal portion of the first prosthesis may be positioned either upstream or downstream of the renal arteries, a downstream portion of the first prosthesis 10 is positioned downstream of the renal arteries. When the upstream portion of the first prosthesis 10 is positioned upstream from the renal arteries, for example, in the infrarenal neck region, an intermediate portion of the first prosthesis is positioned across the junction between the renal arteries and the abdominal aorta. The outward force of the second prostheses 11*a* and 11*b* on the precursor stent 10 helps to secure the device within the body. The downstream ends of the second prostheses 11*a* and 11*b* may be matingly engaged with respective third prosthesis 11*e* and 11*f* preferably in the iliac arteries 1 and 2. Thereafter blood will flow from the abdominal aorta 302, through an exemplary system of the present invention comprising a first prosthesis and two second prostheses 11*a* and 11*b*, two third prostheses 11*e* and 11*f* and a branch leg 11*g* at least into external iliac arteries 123 and 126 and internal iliac artery 124, thereby bypassing the abdominal aortic aneurysm 100 and the common iliac artery aneurysms 207 and 208.

In an alternate exemplary embodiment, the system is further configured with second prostheses 11*a* and 11*b* provided with additional second prostheses 11*c* and 11*d*, respectively. Fluid is directed through additional second prostheses 11*c* and 11*d* into renal arteries 3 and 4.

FIGS. 12*a*-12*d* illustrate the delivery and deployment of second prostheses 11*a* and 11*b* for bypassing the aneurysm. The upstream end of each second prosthesis matingly engages the upstream end of first prosthesis 10 through holes 32 and 33 respectively. As the second prostheses 11*a* and 11*b* are deployed, through precise placement by the operator, respective additional second prostheses 11*c* and 11*d* automatically deploy in such a position as to create a fluid flow path or channel from the main leg of prostheses 11*a* and 11*b* into renal arteries 3 and 4. Holes 34 and 35 are the holes through which additional prostheses 11*c* and 11*d* are positioned.

It is important to note that even though self-expanding stents are utilized, balloons may be utilized to over expand the stents for tacking them into position if necessary.

Although shown and described is what is believed to be the most practical and preferred embodiments, it is apparent that departures from specific designs and methods described and shown will suggest themselves to those skilled in the art and may be used without departing from the spirit and scope of the invention. The present invention is not restricted to the particular constructions described and illustrated, but should be constructed to cohere with all modifications that may fall within the scope of the appended claims.

What is claimed is:

1. A system for bypassing multiple aneurysms comprising:
   a first sealing prosthesis, including an expanding lattice defining a substantially tubular structure with an interior volume and having a proximal end, a distal end, and a plurality of spaced longitudinal legs extending from the lattice;
   a gasket covering the proximal end of the sealing prosthesis and at least a portion of the substantially tubular structure;
   at least two second bypass prostheses matingly engaging and communicating with the sealing prosthesis, each of the second prostheses being configured to bypass a first aneurysm in a first artery and to extend into second arteries downstream of the first aneurysm;
   at least two third bypass prostheses matingly engaging and communicating with the respective at least two second bypass prostheses, the at least two third bypass prostheses being configured to provide fluid flow paths in the second arteries downstream from the first artery and to bypass at least one second aneurysm in one of the second arteries, each of the at least two third bypass prostheses defining substantially, tubular shaped sections with a longitudinal axis and having first and second ends and comprising first, second and third sections, the first section including a plurality of open diamond shaped regions and zig-zag shaped regions, the zig-zag shaped regions being positioned between the open diamond shaped regions and at an end of the first section, the second section including a plurality of open diamond shaped regions and zig-zag shaped regions, the zig-zag shaped regions being positioned between the open diamond shaped regions and at an end of the second section, the third section including a plurality of straight struts extending parallel to the longitudinal axis from one or more apexes of the zig-zag shaped regions at the ends of the first and second sections, the plurality of straight struts are attached only on a single end to one of the first and second sections and in an alternating configuration, one or more of the plurality of straight struts being deformable out of the plane of the longitudinal axis thereby forming a branch leg fitting for establishing a fluid flow channel from at least one of the at least two third bypass prostheses into a third artery, the first, second and third sections comprising a monolithic structure with the plurality of straight struts being independent structures of the plurality of open diamond shaped regions and the zig-zag shaped regions; and
   an extension prosthesis connected to and in fluid communication with the branch leg fitting of the at least one third bypass prosthesis.

2. The system of claim 1 wherein each straight strut is shape set to form a substantially identical angle with respect to a longitudinal axis of the at least one third bypass prosthesis.

3. The system of claim 1 wherein the plurality of straight struts comprising the branch leg fitting are shape set substantially perpendicular to a longitudinal axis of the at least one third bypass prosthesis.

4. The system of claim 1 wherein at least some of the plurality of straight struts are shape set to a different angle than others of the plurality of straight struts.

5. The system of claim 1 further comprising a bifurcated graft having a tubular section surrounding the at least one third bypass prosthesis and an offshoot surrounding the branch leg fitting.

* * * * *